(12) United States Patent
Miyakawa et al.

(10) Patent No.: US 11,491,204 B2
(45) Date of Patent: *Nov. 8, 2022

(54) COMPOSITION COMPRISING POLY I:C AND LAG-3-IGG FUSION PROTEIN

(71) Applicant: CYTLIMIC INC., Tokyo (JP)

(72) Inventors: Tomoya Miyakawa, Tokyo (JP); Shun Doi, Tokyo (JP); Koji Tamada, Yamaguchi (JP)

(73) Assignee: Cytlimic Inc., Tokyo (JP)

( * ) Notice: Subject to any disclaimer, the term of this patent is extended or adjusted under 35 U.S.C. 154(b) by 201 days.

This patent is subject to a terminal disclaimer.

(21) Appl. No.: 16/935,534

(22) Filed: Jul. 22, 2020

(65) Prior Publication Data
US 2021/0000916 A1 Jan. 7, 2021

Related U.S. Application Data

(62) Division of application No. 15/564,604, filed as application No. PCT/JP2016/061463 on Apr. 7, 2016, now Pat. No. 10,842,848.

(30) Foreign Application Priority Data

Apr. 7, 2015 (JP) .................................. 2015-078684
Oct. 5, 2015 (JP) .................................. 2015-198066
Feb. 23, 2016 (JP) .................................. 2016-032046

(51) Int. Cl.

| | |
|---|---|
| *A61K 38/17* | (2006.01) |
| *A61K 38/18* | (2006.01) |
| *A61K 39/00* | (2006.01) |
| *A61K 39/39* | (2006.01) |
| *A61K 45/00* | (2006.01) |
| *A61P 35/00* | (2006.01) |
| *C07K 14/475* | (2006.01) |
| *C07K 19/00* | (2006.01) |
| *A61K 38/00* | (2006.01) |
| *A61P 37/02* | (2006.01) |
| *C12N 15/117* | (2010.01) |

(52) U.S. Cl.
CPC ............ *A61K 38/177* (2013.01); *A61K 38/00* (2013.01); *A61K 38/1709* (2013.01); *A61K 38/18* (2013.01); *A61K 39/00* (2013.01); *A61K 39/0011* (2013.01); *A61K 39/39* (2013.01); *A61K 45/00* (2013.01); *A61K 45/05* (2013.01); *A61P 35/00* (2018.01); *A61P 37/02* (2018.01); *C07K 14/475* (2013.01); *C07K 19/00* (2013.01); *C12N 15/117* (2013.01); *A61K 2039/555* (2013.01); *A61K 2039/55511* (2013.01); *A61K 2039/57* (2013.01); *A61K 2039/585* (2013.01); *C07K 2319/30* (2013.01)

(58) Field of Classification Search
CPC ........ A61K 38/00; A61K 39/39; A61K 38/18; A61K 38/1709; A61K 31/713; A61K 9/1652; C12N 15/117; C07K 14/475; C07K 19/00; C07K 2319/30

See application file for complete search history.

(56) References Cited

U.S. PATENT DOCUMENTS

| | | | |
|---|---|---|---|
| 5,196,523 | A | 3/1993 | Lee |
| 6,410,509 | B1 | 6/2002 | Triebel |
| 2002/0192195 | A1 | 12/2002 | Triebel |
| 2003/0171280 | A1 | 9/2003 | Soderstrom |
| 2004/0063173 | A1 | 4/2004 | Multhoff |
| 2007/0081991 | A1 | 4/2007 | Soderstrom |
| 2007/0087009 | A1 | 4/2007 | Burdin et al. |
| 2009/0035330 | A1 | 2/2009 | Dewerchin |
| 2009/0123460 | A1 | 5/2009 | Noelle et al. |
| 2009/0155308 | A1 | 6/2009 | Moon et al. |
| 2009/0239806 | A1 | 9/2009 | Nishimura et al. |
| 2010/0015101 | A1 | 1/2010 | Sato et al. |
| 2010/0028373 | A1 | 2/2010 | Fujioka et al. |
| 2011/0028403 | A1 | 2/2011 | Le Poole et al. |
| 2013/0202707 | A1 | 8/2013 | All et al. |
| 2013/0217122 | A1 | 8/2013 | Kaplan |
| 2014/0220058 | A1 | 8/2014 | Maeda et al. |
| 2015/0023992 | A1 | 1/2015 | Sette et al. |
| 2015/0285806 | A1 | 10/2015 | Ohtomo et al. |
| 2019/0160168 | A1 | 5/2019 | Seya et al. |
| 2020/0038508 | A1 | 2/2020 | Miyakawa et al. |

FOREIGN PATENT DOCUMENTS

| | | |
|---|---|---|
| CA | 2963909 A1 | 4/2016 |
| CN | 101568550 A | 10/2009 |
| EP | 1002108 | 5/2000 |
| EP | 1002108 B1 | 5/2000 |
| EP | 1750707 | 2/2007 |
| EP | 2214705 | 8/2010 |
| EP | 2214705 B1 | 8/2010 |
| EP | 2572715 A1 | 3/2013 |
| JP | 08-151396 A | 6/1996 |
| JP | 2001-510806 A | 8/2001 |
| JP | 2006-512391 A | 4/2006 |

(Continued)

OTHER PUBLICATIONS

O'Beirne et al., "Generation of functional CD8 T Cells by Human dendritic cells expressing glypican-3 epitopes," Journal of Experimental & Clinical Cancer Research, 2010, 29:48, 11 pages.

(Continued)

*Primary Examiner* — Bridget E Bunner
(74) *Attorney, Agent, or Firm* — Foley & Lardner LLP

(57) ABSTRACT

The present invention provides a medicine containing a Toll-like receptor agonist, LAG-3 protein, a variant or derivative thereof.

5 Claims, 27 Drawing Sheets

Specification includes a Sequence Listing.

(56) References Cited

FOREIGN PATENT DOCUMENTS

| JP | 2007-514725 A | 6/2007 |
|---|---|---|
| JP | 2008-540625 A | 11/2008 |
| JP | 2010-538655 A | 12/2010 |
| JP | 2011-506309 A | 3/2011 |
| RU | 2333767 C2 | 10/2007 |
| WO | WO 99/04810 A2 | 2/1999 |
| WO | WO-00/37504 A2 | 6/2000 |
| WO | WO-01/14424 A2 | 3/2001 |
| WO | WO 2004/018667 A1 | 3/2004 |
| WO | WO 2005/060966 A1 | 7/2005 |
| WO | WO-2006/121168 A1 | 11/2006 |
| WO | WO 2007/018199 A1 | 2/2007 |
| WO | WO 2007/119515 A1 | 10/2007 |
| WO | WO 2008/106491 A2 | 9/2008 |
| WO | WO-2008/156712 A1 | 12/2008 |
| WO | WO-2009/008719 A2 | 1/2009 |
| WO | WO 2009/072767 A2 | 6/2009 |
| WO | WO-2010/077634 A1 | 7/2010 |
| WO | WO 2011/044246 A1 | 4/2011 |
| WO | WO-2011/066389 A1 | 6/2011 |
| WO | WO-2013/079174 A1 | 6/2013 |
| WO | WO 2013/119863 A1 | 8/2013 |
| WO | WO 2013/143026 A1 | 10/2013 |
| WO | WO-2014/097648 A1 | 6/2014 |
| WO | WO 2014/134355 A1 | 9/2014 |
| WO | WO 2015/168379 A2 | 11/2015 |
| WO | WO 2016/056596 A1 | 4/2016 |
| WO | WO 2016/143816 A1 | 9/2016 |
| WO | WO 2016/163489 A1 | 10/2016 |
| WO | WO-2018/021400 A1 | 2/2018 |
| WO | WO-2018/070069 A1 | 4/2018 |

OTHER PUBLICATIONS

Office Action dated Sep. 1, 2020 in Chinese Application No. 201680014548.9, with English translation.
Sun et al., "Immune activity evaluation of GPC3 peptides recognized by HLA-A11 restricted T lymphocytes in hepatocellular carcinoma patients," Beijing Medical Journal, Dec. 31, 2014, 36(9):752-755.
Tada et al., "Analysis of cytotoxic T lymphocytes from a patient with hepatocellular carcinoma who showed a clinical response to vaccination with a glypican-3-derived peptide," International Journal of Oncology, Dec. 31, 2013, 43:1019-1026.
AdipoGen™ Safety Data Sheet, "LAG-3 (mouse):Fc mMouse) (rec)," May 5, 2011, 3 pages.
American Cancer Society, "Non-specific cancer immunotherapies and adjuvants," Aug. 8, 2016, 4 pages.
Ammi et al., "Poly(I:C) as cancer vaccine adjuvant: Knocking on the door of medical breakthroughs," Pharmacology & Therapeutics, 2015, vol. 146, pp. 120-131.
Brignone et al., "A Soluble Form of Lymphocyte Activation Gene-3 (IMP321) Induces Activation of a Large Range of Human Effector Cytotoxic Cells," The Journal of Immunology, 2007, 179:4202-4211.
Ebner et al., "Identification of Multiple T Cell Epitopes on Bet v I, the Major Birch Pollen Allergen, Using Specific T Cell Clones and Overlapping Peptides," The Journal of Immunology, Feb. 1, 1993, 150(3):1047-1054.
Faure et al., "Inducible Hsp70 as Target of Anticancer Immunotherapy: Identification of HLA-A*0201-Restricted Epitopes," Int. J. Cancer, Mar. 1, 2004, 108(6):863-870.
Fougeray et al., "A soluble LAG-3 protein as an immunopotentiator for therapeutic vaccines: Preclinical evaluation of IMP321" Vaccine, Jun. 29, 2006, 24(26):5426-5433.
Fransen et al., "Local immunomodulation for cancer therapy," OncoImmunology, Nov. 1, 2013, 2(11):e26493, 3 pages.
Galluzzi et al., "Trial Watch: Experimental Toll-like receptor agonists for cancer therapy," OncoImmunology, Aug. 1, 2012, 1(5):699-739.

Goldberg et al., "LAG-3 in Cancer Immunotherapy," Curr. Top. Microbiol. Immunol., Jan. 1, 2011, 344:269-278.
Guha, Malini, "Anticancer TLR agonists on the ropes," Nature Reviews Drug Discovery, Jul. 2012, 11(7):503-505.
Harig et al., "Induction of cytotoxic T-cell responses against immunoglobulin V region-derived peptides modified at human leukocyte antigen-A2 binding residues," Blood, Nov. 15, 2001, 98(10):2999-3005.
International Search Report dated Jun. 14, 2016, in PCT/JP2016/057356.
International Search Report dated Jun. 27, 2017, in PCT/JP2017/015227.
International Search Report dated Jun. 28, 2016, in PCT/JP2016/061463.
International Search Report dated Nov. 24, 2015, in PCT/JP2015/078504.
Iwama et al., "Identification of an H2-$K^b$ or H2-$D^b$ restricted and glypican-3-derived cytotoxic T-lymphocyte epitope peptide," International Journal of Oncology, Jan. 23, 2013, 42(3):831-838.
Kano et al., "Combined adjuvants of poly(I:C) plus LAG-3-Ig improve antitumor effects of tumor-specific T cells, preventing their exhaustion," Cancer Sci., Apr. 15, 2016, 107(4):398-406.
Kano et al., "Investigation of Inhibition of Tumor-Specific T Cell Exhaustion by Combination of Adjuvants: poly(I:C) and LAG-3-Ig and its Anti-Tumor Effect," $20^{th}$ Annual Meeting of the Japanese Association of Cancer Immunology, Jul. 28, 2016, O05-4, p. 136, with English translation.
Komori et al., "Identification of HLA-A2- or HLA-A24-Restricted CTL Epitopes Possibly Useful for Glypican-3-Specific Immunotherapy of Hepatocellular Carcinoma," Clin. Cancer Res., May 1, 2006, 12(9):2689-2697.
Li et al., "Lymphocyte Activation Gene-3 Fusion Protein Increases the Potency of a Granulocyte Macrophage Colony-Stimulating Factor-Secreting Tumor Cell Immunotherapy," Clin. Cancer Res., Jun. 1, 2008, 14(11):3545-3554.
Llopiz et al., "Combined immunization with adjuvant molecules poly(I:C) and anti-CD40 plus a tumor antigen has potent prophylactic and therapeutic antitumor effects," Cancer Immunol. Immunother., 2008 (online Jun. 13, 2007), 57:19-29.
Martins et al., "Vaccine adjuvant uses of poly-IC and derivatives," Expert Review of Vaccines, 2015 (online Oct. 13, 2014), 14(3):447-459.
Matsui et al., "HSP70-mRNA-Induced Dendritic Cell Therapy for Hepatocellular Carcinoma (HCC) and Search of New Epitope Peptide therefor," $20^{th}$ Annual Meeting of the Japanese Association of Cancer Immunology, Jul. 28, 2016, O06-5, p. 137, with English translation.
Nakatsura et al., "Mouse Homologue of a Novel Human Oncofetal Antigen, Glypican-3, Evokes T-Cell-Mediated Tumor Rejection without Autoimmune Reactions in Mice," Clinical Cancer Research, Dec. 15, 2004, 10(24):8630-8640.
Office Action dated Aug. 29, 2019, in RU 201735038, with English translation.
Office Action dated Dec. 5, 2018, in U.S. Appl. No. 15/516,918.
Office Action dated Jan. 28, 2019, in U.S. Appl. No. 15/556,694.
Office Action dated Jan. 31, 2020, in TW 105110968.
Office Action dated Mar. 17, 2020, in AU 2016244570.
Office Action dated Oct. 17, 2017, in JP 2017-511073.
Office Action dated Oct. 17, 2019, in TW 104133022.
Office Action dated Sep. 20, 2019, in RU 2017134693, with English translation.
Office Action dated Mar. 23, 2018, in Russian Application No. RU 2017115719, with English translation.
Okochi et al., "Identification of HLA-A24-Restricted Epitopes with High Affinities to Hsp70 Using Peptide Arrays," Journal of Bioscience and Bioengineering, Mar. 2008, 105(3):198-203.
P.H.N. Celie et al., "Crystal structure of MHC CLass I HLA-A2.1 bound to HIV-1 envelope peptide env120-128," RCSB Protein Data Bank, 2010, https://www.rcsb.org/structure/2X4O, 6 pages.
Pan et al., "Interferon-γ is an autocrine mediator for dendritic cell maturation," Immunology Letters, May 26, 2004, 94(1-2):141-151.
Reed et al., "New horizons in adjuvants for vaccine development," Trends in Immunology, Dec. 6, 2008, 30(1):23-32.

(56) References Cited

OTHER PUBLICATIONS

Romano et al., "MART-1 peptide vaccination plus IMP321 (LAG-3Ig fusion protein) in patients receiving autologous PBMCs after lymphodepletion: results of a Phase I trial," Journal of Translational Medicine, Apr. 12, 2014, 12(97):1-12.
Sierro et al., "The CD4-like molecule LAG-3, biology and therapeutic applications," Expert Opin. on Ther. Targets, Jan. 2011, 15(1):91-101.
Supplemental European Search Report dated Jul. 11, 2018, in EP 15849707.3.
Supplementary European Search Report dated Nov. 16, 2018, in EP 16776655.9.
Supplementary Partial European Search Report dated Apr. 13, 2018, in EP 15849707.3.
Talmadge et al., "Immunotherapeutic Potential in Murine Tumor Models of Polyinosinic-Polycytidylic Acid and Poly-L-lysine Solubilized by Carboxymethylcellulose," Cancer Research, Mar. 1985, 45:1066-1072.
Udaka et al., "An automated prediction of MHC class I-binding peptides based on positional scanning with peptide libraries," Immunogenetics, Jul. 8, 2000, 51(10):816-828.
Vacchelli et al., "Trial Watch: Toll-like receptor agonists for cancer therapy," OncoImmunology, Aug. 1, 2013, 2(8):e25238, 14 pages.
White et al., "Cancer Prevention for the Next Generation," Journal of Adolescent Health, 2013, 52:S1-S7.
Wick et al., "Profound CD8+ T cell immunity elicited by sequential daily immunization with exogenous antigen plus the TLR3 agonist poly(I:C)," Vaccine, 2011, 29:984-993.
Zhao et al., "Poly I:C-Induced Tumor Cell Apoptosis Mediated by Pattern-Recognition Receptors," Cancer Biotherapy and Radiopharmaceuticals, 2012, 27(9):530-534.
International Search Report in PCT/JP2020/043938 dated Jan. 26, 2021.
Menon et al., "Advances in Cancer Immunotherapy in Solid Tumors," Cancers, 2016, 8:106, 21 pages.
Pardoll et al., "The blockade of immune checkpoints in cancer immunotherapy," Nature Reviews Cancer, Apr. 2012, 12:252-264.
Wolchok, Jedd D., "PD-1 Blockers," Cell, Aug. 27, 2015, 162:937.
Multhoff et al., "A 14-mer Hsp70 peptide stimulates natural killer (NK) cell activity," Cell Stress & Chaperones, Oct. 1, 2001, 6(4):337-344.
Partial European Search Report dated Oct. 29, 2021, in EP 21174944.5.
Office Action dated Jun. 22, 2021, in CN 201580054234.7, with English translation.
Shang, Wei, Ed., Clinical Bio-Immunotherapy for Tumors, Tianjin Science and Technology Press, Jan. 31, 2006, 284-285, with English translation.
Janeway et al., Eds., Immuno Biology, 6th Edition, 2005, 626-627.
Nakajima et al., "A phase I study of multi-HLA-binding peptides derived from heat shock protein 70/glypican-3 and a novel combination adjuvant of hLAG-3Ig and Poly-ICLC for patients with metastatic gastrointestinal cancers: YNP01 trial," Cancer Immunology, Immunotherapy, Mar. 26, 2020, 1651-1662.
Allowance dated Apr. 7, 2021 in CN 201680014548.9.
Bork et al., "Go hunting in sequence databases but watch out for the traps," Trends in Genetics, 1996, 12:425-427.
Bork et al., "Powers and Pitfalls in Sequence Analysis: The 70% Hurdle," Genome Research, 2000, 10:398-400.
Brenner et al., "Errors in genome annotation," Trends in Genetics, Apr. 1999, 15(4):132-133.
Doerks et al., "Protein annotation: detective work for function prediction," Trends in Genetics, Jun. 1998, 14(6):248-250.
Graydon et al., "LAG3's Enigmatic Mechanism of Action," Frontiers in Immunology, Jan. 8, 2021, 11:615317, 7 pages.
Huard et al., "Characterization of the major histocompatibility complex class II binding site on LAG-3 protein," Proc. Natl. Acad. Sci. USA, May 1997, 94;5744-5749.
Ngo et al., The Protein Folding Problem and Tertiary Structure Prediction, Merz et al., Eds., 1994, 492-495.
Office Action dated May 18, 2021 in U.S. Appl. No. 16/341,415.
Skolnick et al., "From genes to protein structure and function: novel applications of computational approaches in the genomic era," Trends in Biotech., Jan. 2000, 18:34-39.
Smith et al., "The challenges of genome sequence annotation or 'The devil is in the details'," Nature Biotechnology, 1997, 15:1222-1223.
Tokuriki et al,. "Stability effects of mutations and protein evolvability," Current Opinion in Structural Biology, 2009, 19:596-604.
Wells et al., "Additivity of Mutational Effects in Proteins," Biochemistry, Sep. 18, 1990, 29(37):8509-8517.
Belikov, V.G., Vysshaya Shkola, 1993, 43-47.
Jiang et al., "Expression significance of HLA-DR antigen and heat shock protein 70 in hepatocellular carcinoma," World Chinese Journal of Digestology, Oct. 15, 2001, 9(10):1139-1142, with English abstract.
Mashkovsky, M.D., Navaya Volna, 2001, 1(14):11.
Office Action dated May 19, 2020, in RU 2019113989, with English translation.
Office Action dated May 28, 2020, in CN 201580054234.7, with English translation.
Sabbatini et al., "Phase I Trial of Overlapping Long Peptides from a Tumor Self-Antigen and Poly-ICLC Shows Rapid Induction of Integrated Immune Response in Ovarian Cancer Patients," Clinical Cancer Research, 2012, 18(23):6497-6508.
Zhu et al., "Toll like receptor-3 ligand poly-ICLC promotes the efficacy of peripheral vaccinations with tumor antigen-derived peptide epitopes in murine CNS tumor models," Journal of Translational Medicine, Feb. 12, 2007, 5(10):15 pages.

```
SEQUENCE LISTING

<160> NUMBER OF SEQ ID NOS: 2

<210> SEQ ID NO 1
<211> LENGTH: 9
<212> TYPE: PRT
<213> ORGANISM: Mus musculus

<400> SEQUENCE: 1

Leu Pro Tyr Leu Gly Trp Leu Val Phe
1               5

<210> SEQ ID NO 2
<211> LENGTH: 9
<212> TYPE: PRT
<213> ORGANISM: Mus musculus

<400> SEQUENCE: 2

Lys Val Pro Arg Asn Gln Asp Trp Leu
1               5
```

COMPOSITION COMPRISING POLY I:C AND LAG-3-IGG FUSION PROTEIN

CROSS-REFERENCE TO RELATED APPLICATIONS

This application is a Divisional of U.S. application Ser. No. 15/564,604, which is the U.S. National Stage application of PCT/JP2016/061463, filed Apr. 7, 2016, which claims priority from Japanese application nos. JP 2015-078684, filed Apr. 7, 2105, JP 2015-198066, filed Oct. 5, 2015, and JP 2016-032046, filed Feb. 23, 2016.

The instant application contains a Sequence Listing which has been submitted in ASCII format via EFS-WEB and is hereby incorporated by reference in its entirety. Said ASCII copy, created on Jul. 14, 2020, is named sequence.txt and is 669 bytes.

TECHNICAL FIELD

The present invention relates to a medicine or the like containing a Toll-like receptor agonist and LAG-3 protein, a variant or derivative thereof.

BACKGROUND ART

Recently, cancer immunotherapies targeting cancer antigens expressed specifically in cancer cells have been developed. Of them, a "cancer vaccine therapy" is a method of inducing regression of cancer by administering a cancer antigen directly to patients to induce an immune response specific to a cancer antigen in the patient's body. As the cancer antigen to be administered to a patient, e.g., a cancer-antigen protein itself, a cancer-antigen derived peptide, a nucleic acid encoding them, a dendritic cell presenting a cancer antigen and a cancer cell itself, are used.

To enhance induction of an immune response by a cancer antigen, an adjuvant is administered together with the cancer antigen. As the adjuvant, e.g., cytokines stimulating various immunocompetent cells and Toll-like receptor (TLR) agonists are used.

As the TLR agonist serving as an adjuvant, any one of TLR1 to TLR10 agonists can be used (for example, Non Patent Literatures 1 and 2). For example, TLR3, which recognizes virus-derived double-stranded RNA and accelerates production of type I interferon exerting a strong antiviral action, is a molecule of the innate immune system. A double-stranded RNA analogue, Poly I:C (also called as Polyinosinic:polycytidylic acid), which is known as a TLR3 agonist, is known to be used as a vaccine adjuvant (for example, Patent Literature 1). Also, TLR9, which recognizes a bacterium- or virus-derived unmethylated CpG DNA and exerts an action, is a molecule of the innate immune system. CpG ODN (synthetic nucleic acid CpG oligodeoxynucleotide) serving as a TLR9-ligand is known to have an adjuvant effect for vaccine.

It is known that LAG-3 is also used as an adjuvant for vaccine (for example, Patent Literature 2). LAG-3 is a posttranslational product of lymphocyte activation gene 3 and also called as CD223. LAG-3 binds to a MHC Class II molecule to negatively control proliferation of activated T cells and homeostasis maintenance of T cells, plays an important role in regulatory T cell (Treg) function and is also known to be involved in homeostatic regulation of plasmacytoid dendritic cells.

CITATION LIST

Patent Literature

Patent Literature 1: National Publication of International Patent Application No. 2011-506309
Patent Literature 2: National Publication of International Patent Application No. 2001-510806

Non Patent Literature

Non Patent Literature 1: OncoImmunology 1: 5, 699-716; August 2012
Non Patent Literature 2: OncoImmunology 2: 8, e25238; August 2013

SUMMARY OF INVENTION

Technical Problem

An object of the present invention is to provide a medicine containing a novel combination of adjuvants.

Solution to Problem

The present inventors conducted various studies using various adjuvants singly or in combination. As a result, they found a novel combination of adjuvants serving as a medicine useful for, for example, inducing cancer immunity.

More specifically, the present invention is as follows.

[1]
A medicine comprising
a Toll-like receptor agonist and
LAG-3 protein, a variant or derivative thereof.
[2]
The medicine according to [1] for combined administration of
the Toll-like receptor agonist and
LAG-3 protein, a variant or derivative thereof.
[3]
The medicine according to [1] or [2], wherein the Toll-like receptor agonist is Toll-like receptor 3 agonist or a Toll-like receptor 9 agonist.
[4]
The medicine according to any one of [1] to [3], in which the Toll-like receptor agonist is Poly I:C or a salt thereof.
[5]
The medicine according to any one of [1] to [4], wherein the LAG-3 protein, a variant or derivative thereof is a fusion protein of LAG-3 protein and IgG.
[6]
The medicine according to any one of [1] to [5], further comprising a substance for inducing a specific immune response to at least one cancer cell.
[7]
The medicine according to [6], for combined administration of
the Toll-like receptor agonist,
LAG-3 protein, a variant or derivative thereof, and
the substance for inducing a specific immune response to at least one cancer cell.
[8]
The medicine according to [6] or [7], wherein the substance for inducing a specific immune response to a cancer cell is a cancer-antigen derived peptide.

[9]

The medicine according to [8], comprising two or more cancer-antigen derived peptides.

[10]

The medicine according to any one of [1] to [9], for use in a cancer vaccine therapy.

[11]

The medicine according to any one of [1] to [10], wherein the medicine is an anti-cancer agent.

[12]

An adjuvant comprising a Toll-like receptor agonist and

LAG-3 protein, a variant or derivative thereof, for use in inducing a specific immune response to a cancer cell or for use in a cancer vaccine therapy.

[13]

A combination comprising a Toll-like receptor agonist and

LAG-3 protein, a variant or derivative thereof, for use in inducing a specific immune response to a cancer cell or in a cancer vaccine therapy.

[14]

A method for treating or preventing a disease in a patient, comprising administering a Toll-like receptor agonist and LAG-3 protein, a variant or derivative thereof to a patient in need thereof.

[15]

A method for inducing a specific immune response, comprising administering a Toll-like receptor agonist and LAG-3 protein, a variant or derivative thereof to a patient in need thereof.

Advantageous Effects of Invention

According to the present invention, it is possible to provide a medicine containing a new combination of adjuvants.

DESCRIPTION OF EMBODIMENTS

Figure 1:
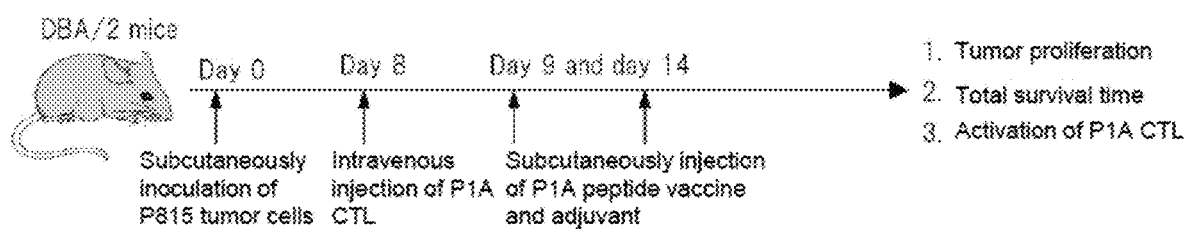
FIG. 1 shows a schematic protocol of an experiment for comparing effects of adjuvants in a cancer vaccine using a cancer-antigen derived peptide.
Figure 2:
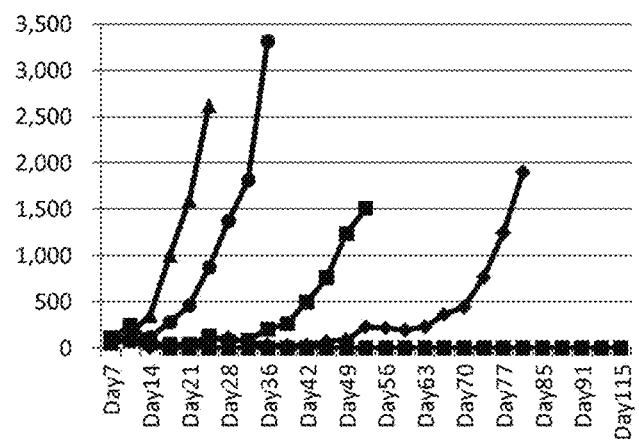
FIG. 2 is a graph showing changes in tumor size of Group 1, in which PBS was used as a control in the experiment of FIG. 1.
Figure 3:
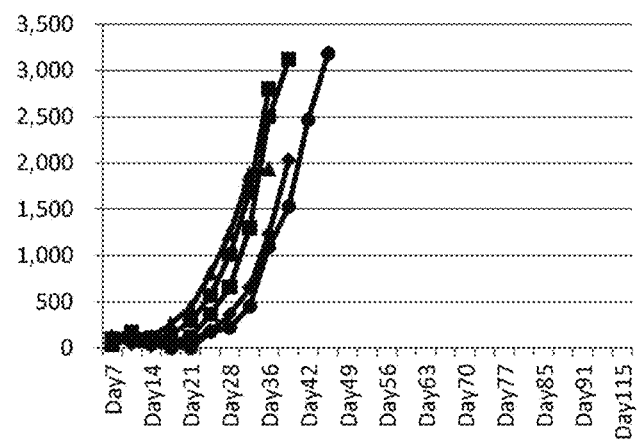
FIG. 3 is a graph showing changes in tumor size in Group 2, in which IFA was used as an adjuvant in the experiment of FIG. 1.
Figure 4:
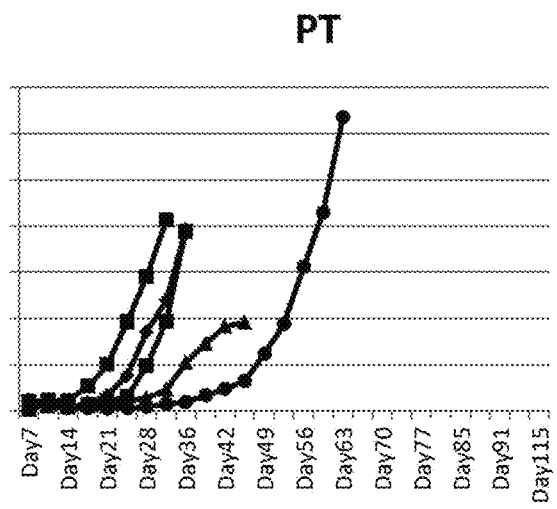
FIG. 4 is a graph showing changes in tumor size in Group 3, in which PT was used as an adjuvant in the experiment of FIG. 1.
Figure 5:
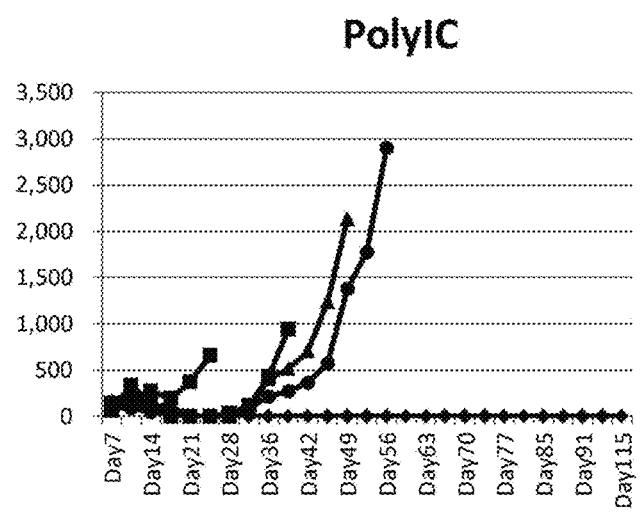
FIG. 5 is a graph showing changes in tumor size in Group 4, in which Poly I:C was used as an adjuvant in the experiment of FIG. 1.
Figure 6:
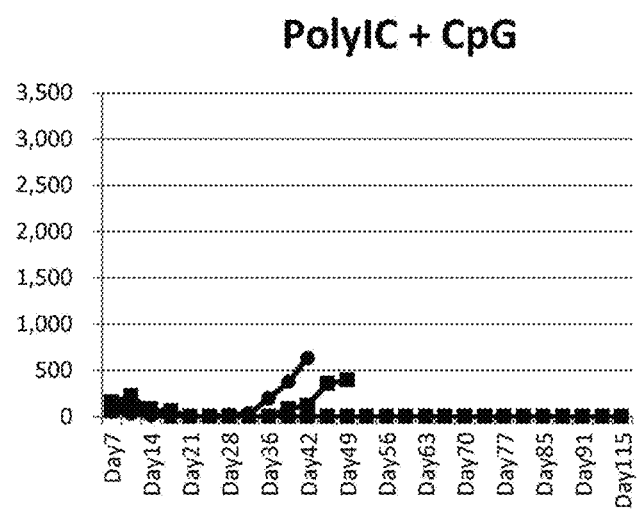
FIG. 6 is a graph showing changes in tumor size in Group 5, in which a combination of Poly I:C and CpG was used as an adjuvant in the experiment of FIG. 1.
Figure 7:
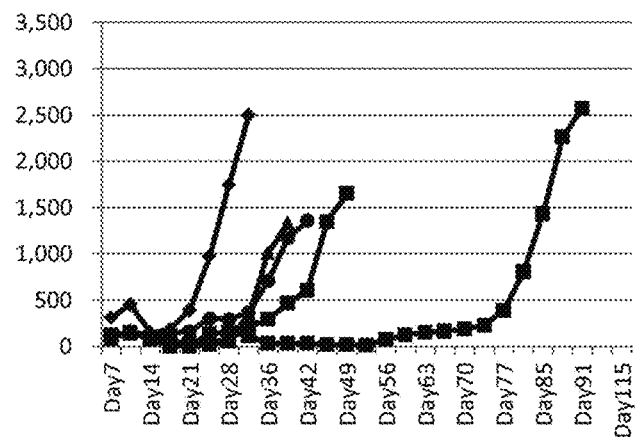
FIG. 7 is a graph showing change in tumor size in Group 6, in which LAG-3 was used as an adjuvant in the experiment of FIG. 1.
Figure 8:
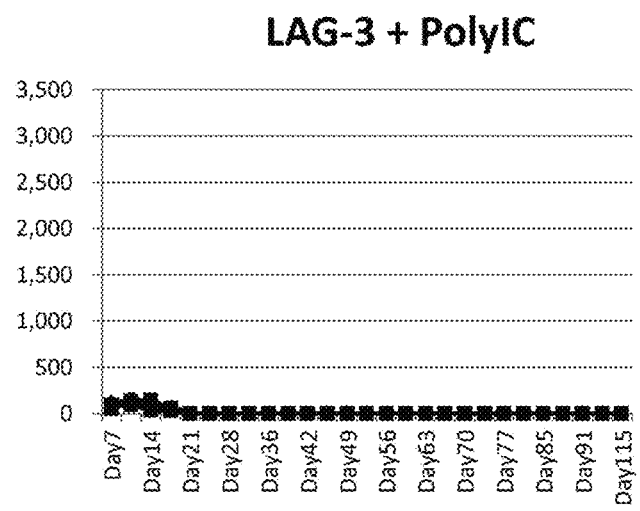
FIG. 8 is a graph showing change in tumor size in Group 7, in which LAG-3 and Poly I:C were used as adjuvants in the experiment of FIG. 1.

The present invention will be more specifically described below by way of embodiments; however, the present invention is not limited to the embodiments and can be modified in various ways and carried out.

A medicine according to the present invention includes a Toll-like receptor agonist (TLR agonist) and LAG-3 protein, a variant or derivative thereof.

In the specification, the "Toll-like receptor agonist (TLR agonist)" refers to a molecule, which binds to any one of Toll-like receptors and provides the same stimulus as the stimulus provided by a natural ligand bound to TLR. As the TLR agonist, TLP agonists described in Trends in Immunology Vol. 30 No. 1, 23-32, Immunity 33, Oct. 29, 2010, 492-503, and World Journal of Vaccines, 2011, 1, 33-78, are known. These TLRs known in the art each can be used in the TLR agonist of the present invention; for example, a TLR3 agonist, TLR4 agonist, TLR7 agonist, TLR8 agonist, TLR9 agonist or TLR10 agonist can be used. Of them, a TLR3 agonist or TLR9 agonist may be used as the TLR agonist.

In the specification, the "TLR3 agonist" refers to a molecule which binds to TLR3 and provides the same stimulus as the stimulus provided by a natural ligand bound to TLR3. TLR3 recognizes a virus-derived double stranded RNA to activate the innate immune system. As the TLR3 agonist, a synthetic double stranded polynucleotide, Poly I:C, having an analogous structure to double stranded RNA is known; however, the TLR3 agonist is not limited to this. A salt of Poly I:C may be used in the present invention; for example, a sodium salt thereof can be used. As the TLR3 agonist, RIBOXXOL can be used.

In the specification, the "TLR4 agonist" refers to a molecule which binds to TLR4 and provides the same stimulus as the stimulus provided by a natural ligand bound to TLR4. TLR4 recognizes a bacterium-derived lipopolysaccharide (LPS) to activate the innate immune system. As the TLR4 agonist, MPL is known; however, the TLR4 agonist is not limited to this. A salt of MPL may be used in the present invention; for example, a sodium salt thereof can be used.

In the specification, the "TLR5 agonist" refers to a molecule which binds to TLR5 and provides the same stimulus as the stimulus provided by a natural ligand bound to TLR5. TLR5 recognizes a bacterium-derived Flagellin to activate the innate immune system. As the TLR5 agonist, Flagellin (proteins) derived from various bacteria or recombinant Flagellin proteins are known; however, the TLR5 agonist is not limited to these.

In the specification, the "TLR7 agonist" refers to a molecule which binds to TLR7 and provides the same stimulus as the stimulus provided by a natural ligand bound to TLR7.

Also, in the specification, the "TLR8 agonist" refers to a molecule which binds to TLR8 and provides the same stimulus as the stimulus provided by a natural ligand bound to TLR8.

TLR7 and TLR8 recognize virus-derived single stranded RNA to activate the innate immune system. As the TLR7/8 agonist, Imiquimod is known; however, the TLR7/8 agonist is not limited to this. A salt of Imiquimod may be used in the present invention; for example, a sodium salt thereof can be used.

In the specification, the "TLR9 agonist" refers to a molecule which binds to TLR9 and provides the same stimulus as the stimulus provided by a natural ligand bound to TLR9. TLR9 recognizes bacterium- and virus-derived CpG DNA to activate the innate immune system. As the TLR9 agonist, CpG ODN is known; however, the TLR9 agonist is not limited to this. A salt of CpG ODN may be used in the present invention; for example, a sodium salt thereof can be used.

In the specification "LAG-3 protein, a variant or derivative thereof" refers to LAG-3 protein, a functional variant or derivative thereof. The LAG-3 protein to be used in the present invention may be derived from any animal, for example, the protein can be derived from the same animal as the subject to which a medicine according to the present invention is to be administered. More specifically, if a medicine according to the present invention is administered to a human, human LAG-3 can be used. Human LAG-3 protein is a protein having an amino acid sequence represented by NCBI Accession No. P18627.5.

Examples of the functional variant of LAG-3 protein include, (i) an LAG-3 variant consisting of an amino acid sequence, which is the amino acid sequence of LAG-3 having addition, substitution, or deletion of one or several amino acids and having a function of LAG-3 protein required for exerting the effects of the present invention, (ii) an LAG-3 variant having a sequence identity with the amino acid sequence of LAG-3 of at least 80% or more, or 85% or more, 90% or more, 95% or more, 98% or more or 99% or more and having a function of LAG-3 protein required for exerting the effects of the present invention, and (iii) a partial polypeptide of LAG-3 protein, a variant defined in the above (i) or a variant defined in the above (ii) having a function of LAG-3 protein required for exerting the effects of the present invention.

In the specification, the "one or several amino acids" refers to 1, 2, 3, 4, 5, 6, 7, 8, 9, or 10 amino acids.

In the specification, the "amino acid" is used in the broadest sense thereof and includes natural amino acids and artificial amino acid variants and derivatives. In the specification, examples of the amino acid include natural protein L-amino acids; D-amino acids; chemically modified amino acids such as amino acid variants and derivatives; natural non-protein amino acids such as norleucine, β-alanine and ornithine; and chemically synthesized compounds having amino acid characteristics known in the art. Examples of non-natural amino acids include α-methyl amino acid (e.g., α-methylalanine), D-amino acid, histidine-like amino acid (e.g., β-hydroxy-histidine, homohistidine, α-fluoromethyl-histidine and α-methyl-histidine), amino acids with extra methylene in a side chain ("homo" amino acids) and amino acids (e.g., cysteine acid) in which the carboxylic acid functional group amino acid in a side chain is substituted with a sulfonic acid group.

Examples of the functional derivative of LAG-3 protein include a fusion protein of all or part of LAG-3 protein and another protein or a polypeptide, and LAG-3 protein attached with a sugar chain and/or a lipid. As an example of the functional derivative of LAG-3 protein, a fusion protein of LAG-3 and IgG. Examples of the functional derivative of LAG-3 protein include the derivatives described in Journal of Translational Medicine 2014, 12: 97.

A medicine according to the present invention may contain a TLR agonist, LAG-3 protein, a variant or derivative thereof and a substance for inducing a specific immune response to a cancer cell.

In the specification, the "substance for inducing a specific immune response to a cancer cell" is not particularly limited as long as it is a substance capable of inducing an immune response necessary for breaking cancer cells in-vivo and inducing apoptosis of cancer cells; for example, a cancer-antigen protein, a cancer-antigen derived peptide, nucleic acids encoding them, a cancer antigen-presenting cell and a tumor cell itself are mentioned.

In the specification, the "cancer-antigen protein" is a protein specially expressed on a cancer cell and recognized/attacked by the immune system as a foreign body. The "cancer-antigen protein" may be expressed on cancer cells of all types and a specific type of cancer. As the cancer-antigen protein, a protein having strong immunogenicity and never be expressed in normal cells, is preferable. Examples of the cancer-antigen protein include, but are not particularly limited to, those described in Clin Cancer Res 2009; 15 (17) 5323. Specific examples thereof include, but are not particularly limited to, WT1, MUC1, LMP2, HPVE6, HPVE7, EGFRv III, HER-2/neu, MAGE-A3, p53nonmutant, HSP70, GPC3, MUC1, Casp8, CDAM1, cMyb, EVC1, EVC2, Helios, Fas, NY-ESO-1, PSMA, GD2, CEA, MelanA/MART1, Ras mutant, gp100, p53 mutant, Proteinase3 (PR1), bcr-abl, Tyrosinase, Survivin, PSA, hTERT, Sarcoma translocation breakpoints, EphA2, PAP, ML-IAP, AFP, EpCAM, ERG, NA17, PAX3, ALK, Androgen receptor, Cyclin B1, Polysialic acid, MYCN, PhoC, TRP-2, GD3, Fucosyl GM1, Mesothelin, PSCA, MAGE A1, sLe, CYP1B1, PLAC1, GM3, BORIS, Tn, GloboH, ETV6-AML, NY-BR-1, RGS5, SART3, STn, Carbonic anhydrase IX, PAX5, OY-TES1, Sperm protein 17, LCK, HMWMAA, AKAP-4, SSX2, XAGE1, B7H3, Legumain, Tie2, Page4, VEGFR2, MAD-CT-1, FAP, PDGFR, MAD-CT-2 and Fos-related antigen 1.

In the specification, the "cancer-antigen derived peptide" refers to a peptide having a part of the amino acid sequence of a cancer-antigen protein, or a peptide having a sequence, which is the same amino acid sequence as above and having addition, substitution or deletion of 1 or 2 amino acids, or a peptide having a sequence identity with the above amino acid sequence of 90% or more, 95% or more, 98% or more, or 99% or more and inducing immune which attacks cancer cells. The cancer-antigen derived peptide may consist of amino acid residues of 8 or more and 11 or less. Such a peptide, if it is subcutaneously administered to a patient, is incorporated into antigen-presenting cells, such as dendritic cells and macrophages, and presented on the surface of the cells together with HLA molecules. Precursor cells of cytotoxic T cell (CTL) having a reactivity to the peptide presented are clonally proliferated and mature CTLs that proliferated and differentiated migrate through the lymph flow into a cancer tissue. The mature CTLs attack a cancer cell on which a peptide having the same sequence as the peptide administered is expressed to induce apoptosis.

In the specification, the "nucleic acid" is not particularly limited as long as it is a nucleic acid encoding a cancer-antigen protein or a cancer-antigen derived peptide, and includes RNA, DNA, PNA, LNA or a chimeras of two or more of these. These nucleic acids can be inserted into, e.g., a vector, in accordance with a known method, and then administered to patients and express a cancer-antigen protein or a cancer-antigen derived peptide, in vivo.

In the specification, the "cancer antigen-presenting cell" refers to an antigen-presenting cell presenting a cancer-antigen derived peptide on the surface thereof via binding to an HLA molecule. As the antigen-presenting cell, dendritic cells and macrophages can be used. The dendritic cells have particularly high CTL inducibility. The antigen-presenting dendritic cells can be obtained, for example, by separating mononuclear cells from the patient's own peripheral blood, differentiating the mononuclear cells into immature dendritic cells and thereafter further differentiating mature dendritic cells by adding a cancer-antigen protein or a cancer-antigen derived peptide to a medium.

As a cancer vaccine presently under development, vaccines using dendritic cells sensitized with a tumor cell extract, dendritic cells sensitized with a cancer antigen/GM-CSF fusion protein and a combination of noninfectious virus-like particles of a HPV-derived L1 protein and an adjuvant, are known. These are included in the "substance for inducing a specific immune response to a cancer cell".

A medicine according to the present invention may contain at least two types of "substances inducing a specific immune response to a cancer cell". For example, a medicine according to the present invention can contain two or more different cancer-antigen derived peptides.

A medicine according to the present invention can be used as a cancer vaccine therapy. In this case, a TLR agonist and LAG-3 protein, a variant or derivative thereof serve as adjuvants and enhance induction of an immune response by a "substance for inducing a specific immune response to a cancer cell". As shown in Examples (later described), when the TLR agonist and LAG-3 protein are used in combination, an extremely high antitumor effect can be obtained even at a low dose at which no effect is obtained when they are used alone.

In the specification, the "adjuvant" refers to a molecule(s), which is administered together with a substance for inducing an immune response to enhance induction of the immune response.

A cancer vaccine therapy can be used for prevention or treatment of cancer. In the specification, prevention or treatment of cancer refers to causing at least one of phenomenon: a decrease in tumor size, delay or termination of increase in tumor size, inhibition (delay or termination) of cancer metastasis, inhibition (delay or termination) of proliferation of cancer cells, inhibition (delay or termination) of cancer recurrence, and mitigation of one or more of symptoms associated with cancer.

In the specification, the term "cancer" is used in the broadest sense thereof. Examples of the cancer include, but are not limited to, astrocytoma, oligodendroglioma, meningioma, neurofibroma, glioblastoma, ependymoma, neurilemmoma, neurofibrosarcoma, neuroblastoma, pituitary tumor (for example, for pituitary adenoma), medulloblastoma, melanoma, brain tumor, prostate cancer, head and neck cancer, esophageal cancer, renal cancer, renal cell carcinoma, pancreatic cancer, breast cancer, lung cancer, colon cancer, colorectal cancer, stomach cancer, skin cancer, ovarian cancer, bladder cancer, fibrosarcoma, squamous cell carcinoma, neuroectodermal tumor, thyroid tumor, lymphoma, leukemia, multiple myeloma, hepatocellular carcinoma, mesothelioma and epidermoid carcinoma.

The present invention includes an adjuvant including a TLR agonist and LAG-3 protein, a variant or derivative thereof, for use in a cancer vaccine therapy. The TLR agonist is an adjuvant to be administered in combination with LAG-3 protein, a variant or derivative thereof; whereas LAG-3 protein, a variant or derivative thereof can be an adjuvant to be administered in combination with the TLR agonist. Such adjuvants may be administered to a patient together with various "substances inducing a specific immune response to a cancer cell". The term "together" used herein does not mean concurrent administration but means that a TLR agonist and LAG-3 protein, a variant or derivative thereof are administered to a patient such that the TLR agonist and LAG-3 protein, a variant or derivative thereof can function as adjuvants in accordance with a cancer vaccine therapy, in vivo (of a patient's body) and ex vivo.

In the present invention, a medicine containing a TLR agonist for combined administration with LAG-3 protein, a variant or derivative thereof may be provided; or a medicine containing LAG-3 protein, a variant or derivative thereof for combined administration with a TLR agonist may be provided.

Also, in the present invention, a medicine containing a TLR agonist for combined administration with a substance for inducing a specific immune response to a cancer cell and LAG-3 protein, a variant or derivative thereof may be provided. The medicine containing a TLR agonist can act, with LAG-3 protein, a variant or derivative thereof as adjuvants, to enhance induction of immune response by a substance for inducing a specific immune response to a cancer cell, preferably, a cancer-antigen derived peptide. In the present invention, a medicine containing LAG-3 protein, a variant or derivative thereof for combined administration with a substance for inducing a specific immune response to a cancer cell and a TLR agonist may be provided. The medicine containing LAG-3 protein, a variant or derivative thereof can act, with a TLR agonist as adjuvants, to enhance induction of immune response by a substance for inducing a specific immune response to a cancer cell, preferably a cancer-antigen derived peptide.

In a medicine containing a TLR agonist and LAG-3 protein, a variant or derivative thereof according to the present invention, the TLR agonist and LAG-3 protein, a variant or derivative thereof can be used as active ingredients of the medicine. The medicine containing a TLR agonist and LAG-3 protein, a variant or derivative thereof as active ingredients according to the present invention, as shown in Examples (described later), can be used as an anti-cancer agent having a high antitumor effect. In the specification, the "anti-cancer agent" refers to an agent that can be used for preventing or treating cancer. The medicine serving as an anti-cancer agent may contain a TLR agonist and LAG-3 protein, a variant or derivative thereof as active ingredients, and may further contain a substance for inducing a specific immune response to a cancer cell.

In the present invention, a medicine serving as an anti-cancer agent contains a substance for inducing a specific immune response to a cancer cell, preferably, a cancer-antigen derived peptide, as an active ingredient, and may contain a TLR agonist and LAG-3 protein, a variant or derivative thereof as adjuvants.

Components of a medicine according to the present invention are dissolved in a water-soluble solvent to prepare pharmaceutically acceptable salts and a preparation containing the components in the salt form can be administered to patients. Examples of such pharmaceutically acceptable salts include physiologically acceptable water-soluble salts such as a sodium salt, a potassium salt, a magnesium salt and a calcium salt, which are adjusted to have physiological pH by a buffer. Other than water-soluble solvents, a nonaqueous solvent can be used. Examples of the nonaqueous solvent include alcohols such as ethanol and propylene glycol.

A medicine according to the present invention can be used as a pharmaceutical composition, which has any dosage form orally or parenterally administrated. The dosage form is not particularly limited. Examples of the dosage form of a pharmaceutical composition can include a liquid (for example, an injection), a dispersant, a suspension, a tablet, a pill, a powdered drug, a suppository, a powder, a fine grain, a granule, a capsule, syrup, a nasal drop and an ear drop.

A medicine according to the present invention, if it is used as a cancer vaccine, can be orally or parenterally administered. As parenteral administration, for example, intraperitoneal administration, subcutaneous administration, intradermal administration, intramuscular administration, intravenous administration or intranasal administration can be employed.

A preparation of a medicine according to the present invention can be produced in accordance with a method known in the art. In the preparation of a medicine according to the present invention, pharmaceutically acceptable carriers and additives (such as an excipient, a binder, a dispersant, a disintegrant, a lubricant, a solvent, a solubilizer, a coloring agent, a flavoring agent, a stabilizer, an emulsifier, a suspending agent, an absorption promoter, a surfactant, a pH adjustor, a preservative and an antioxidant) may be used. Examples of the carriers and additives include pharmaceutically acceptable organic solvents such as water, saline, a phosphate buffer, dextrose, glycerol and ethanol, collagen, polyvinyl alcohol, polyvinylpyrrolidone, a carboxyvinyl polymer, sodium carboxymethylcellulose, sodium polyacrylate, sodium alginate, water-soluble dextran, sodium carboxymethyl starch, pectin, glutamic acid, aspartic acid, methylcellulose, ethylcellulose, hydroxypropylcellulose, hydroxypropylmethylcellulose, xanthan gum, gum arabic, casein, agar, polyethylene glycol, diglycerin, glycerin, propylene glycol, vaseline, paraffin, stearyl alcohol, stearic acid, human serum albumin, mannitol, sorbitol, lactose, glucose, corn starch, microcrystalline cellulose, a surfactant, sodium bisulfite, sodium bisulfate, sodium thiosulfate, benzalkonium chloride, chlorobutanol, thimerosal, phenylmercuric acetate, phenylmercuric nitrate, methyl paraben, phenylethyl alcohol, ammonia, dithiothreitol, beta mercaptoethanol, sodium carbonate, sodium borate, sodium phosphate, sodium acetate, sodium bicarbonate, sucrose, powdered sugar, sucrose, fructose, glucose, lactose, reduced malt sugar syrup, powdered reduced malt sugar syrup, glucose fructose syrup, fructose glucose sugar, honey, erythritol, aspartame, saccharin, saccharin sodium and gelatin.

When a medicine according to the present invention contains a peptide, an absorption enhancer for improving absorption of a poorly absorbable drug (hard-to-transmucosally absorbed drug), such as a peptide, may be used. Examples thereof include surfactants such as a polyoxyethylene lauryl ether, sodium lauryl sulfate and saponin; bile salts such as glycocholic acid, deoxycholic acid and taurocholic acid; chelating agents such as EDTA and salicyl bile salt; fatty acids such as caproic acid, capric acid, lauric acid, oleic acid, linoleic acid and mixed micelle; an enamine derivative, a N-acyl collagen peptide, a N-acyl amino acid, a cyclodextrin, a chitosan and a nitric oxide donor.

When a medicine according to the present invention contains a peptide, the medicine is encapsulated in e.g., polylactic acid/glycolic acid (PLGA) microcapsules or allowed to adsorb to porous hydroxyapatite fine particles to prepare a sustained release medicine, or the medicine is applied to a pulsed release iontophoresis patch system to prepare a transdermal absorbent.

A medicine according to the present invention may be a single preparation containing a TLR agonist and LAG-3 protein, a variant or derivative thereof or may be a combination of different preparations, i.e., a preparation containing a TLR agonist and a preparation containing LAG-3 protein, a variant or derivative thereof.

Also a medicine according to the present invention may be a single preparation containing a substance for inducing a specific immune response to a cancer cell, a TLR agonist and LAG-3 protein, a variant or derivative thereof or may be a combination of different preparations, i.e., a preparation containing a substance for inducing a specific immune response to a cancer cell, a preparation containing a TLR agonist, and a preparation containing LAG-3 protein, a variant or derivative thereto. More specifically, a preparation containing two types of components selected from a substance for inducing a specific immune response to a cancer cell, a TLR agonist and LAG-3 protein, a variant or derivative thereof may be used in combination with a preparation containing the other remaining component. As long as a combination of three types of components is provided, a preparation containing any two types of components and a preparation containing any two types of components, may be used in combination.

A medicine according to the present invention may be provided in kit form. In the case of a kit, the kit may contain a TLR agonist and LAG-3 protein, a variant or derivative thereof, or may contain a substance for inducing a specific immune response to a cancer cell, a TLR agonist and LAG-3 protein, a variant or derivative thereof.

A medicine according to the present invention, if it is used as a cancer vaccine, may contain additional adjuvants. Non-limiting examples of the additional adjuvants include sedimentary adjuvants such as aluminum hydroxide, sodium hydroxide, aluminum phosphate, calcium phosphate, alum and carboxyvinyl polymer, and oily adjuvants such as Freund's complete adjuvant, Freund's incomplete adjuvant, liquid paraffin, lanolin, montanide ISA763AV and montanide ISA51.

A medicine according to the present invention may be used in combination with other anti-cancer agents in any embodiment and may be used in combination with a radiation therapy and a surgical treatment. Examples of other anti-cancer agent include low molecular compounds such as adriamycin, daunomycin, mitomycin, cisplatin, vincristine, epirubicin, methotrexate, 5-fluorouracil, aclacinomycin, nitrogen mustard, cyclophosphamide, bleomycin, daunorubicin, doxorubicin, vincristine, vinblastine, vindesine, tamoxifen, and dexamethasone; and proteins such as cytokines activating immunocompetent cells (for example, human interleukin 2, human granulocyte macrophage colony stimulating factor, human macrophage colony stimulating factor, and human interleukin 12).

The present invention includes a method for treating cancer by administering a medicine according to the present invention in a therapeutically effective dose. The therapeutically effective dose can be appropriately determined by those skilled in the art depending upon e.g., the symptoms, age, sex, body weight and sensitivity difference of the patient, the administration method, the administration interval and type of preparation.

In the present invention, it is possible to treat or prevent a patient's disease by administering a TLR agonist and LAG-3 protein, a variant or derivative thereof to a patient in need thereof. In the present invention, a method for inducing a specific immune response to a cancer cell by administering a TLR agonist and LAG-3 protein, a variant or derivative thereof, to a patient in need thereof, is provided.

In treating or preventing a patient's disease or in a method for inducing a specific immune response to a cancer cell, a substance for inducing a specific immune response to a cancer cell, preferably, a cancer-antigen derived peptide, may be further administered.

A medicinal effect of a substance for inducing a specific immune response to a cancer cell, preferably a cancer-antigen derived peptide, can be more strongly exerted by inducing a specific immune response to a cancer cell.

A medicine according to the present invention is preferably used for combined administration.

The use of a medicine according to the present invention in combined administration means that a TLR agonist and LAG-3 protein, a variant or derivative thereof may be administered to a patient in any combination at the same time or different times. If a medicine according to the present invention contains a substance for inducing a specific immune response to a cancer cell, the substance for inducing a specific immune response to a cancer cell, a TLR agonist and LAG-3 protein, a variant or derivative thereof may be administered in any combination at the same time or different times.

In administering components at the same time, the components may be administered in single dosage form at the same time; more specifically, a TLR agonist and LAG-3 protein, a variant or derivative thereof may be mixed at the time of administration to prepare a dosing preparation and administered at the same time.

In administering components at different times, a TLR agonist is administered, and thereafter, LAG-3 protein, a variant or derivative thereof may be administered; or LAG-3 protein, a variant or derivative thereof is administered and thereafter a TLR agonist may be administered.

In administering components at the same time if a medicine according to the present invention contains a substance for inducing a specific immune response to a cancer cell, the components may be administered in single dosage form at the same time; more specifically, the substance for inducing a specific immune response to a cancer cell, a TLR agonist and LAG-3 protein, a variant or derivative thereof may be mixed at the time of administration to prepare a dosing preparation and administered at the same time.

In administering components at different times, the substance for inducing a specific immune response to a cancer cell is administered, and thereafter, a TLR agonist and LAG-3 protein, a variant or derivative thereof are administered at the same time or different times; or the TLR agonist and LAG-3 protein, a variant or derivative thereof may be administered at the same time or different times, and thereafter, the substance for inducing a specific immune response to a cancer cell may be administered. Alternatively, one of the TLR agonist and LAG-3 protein, a variant or derivative thereof is administered, and thereafter, the substance for inducing a specific immune response to a cancer cell is administered, and then, the other one of the TLR agonist and the LAG-3 protein, a variant or derivative thereof, may be administered. In administering the components at different times, the components may be administered based on the properties and the dose interval of individual components, in other words, based on the dosing regimens of the individual components.

The disclosures of all Patent Literatures and Non Patent Literatures cited in the specification are incorporated herein in their entirety by reference.

Example 1

Now, the present invention will be described based on Example; however, the present invention is not limited to this. The present invention can be modified in various ways by those skilled in the art without departing from the scope of the present invention and such modification is included in the scope of the present invention.

1. Cancer Vaccine

In accordance with the protocol shown in FIG. 1, the effects of adjuvants in cancer vaccines using a cancer-antigen derived peptide were compared.

Material

As cancer model mice, DBA/2 mice, to which P815 cells (DBA/2mouse-derived mouse mastocytoma) were grafted, were put in use.

As a cancer-antigen derived peptide, a peptide (hereinafter referred to as "P1A peptide") consisting of a partial sequence of P1A protein was used, which is a tumor antigen of P815 tumor and known to be restrictively presented by an MHC H-2Ld. The amino acid sequence of P1A peptide are represented by LPYLGWLVF (SEQ. ID No: 1).

As P1A CTL, a T cell expressing a T cell receptor and recognizing P1A peptide was used. In the experiment, the spleen was taken out from a P1A-CTL transgenic mouse that the present inventors possessed and a positive ratio was checked by TCR Vα 8.3 (TCR marker obtained by gene introduction). Based on the positive ratio, the number of P1A-CTL cells was determined and administered.

As the adjuvants, the following substances were used.
Whole pertussis bacterial cell (PT) (BioFarma, Bandung, Indonesia)
Poly I:C (TLR3 agonist) (Invivogen, SanDiego, USA)
CpG (TLR9 agonist) (Invivogen, SanDiego, USA)
IFA (incomplete Freund's adjuvant) (Seppic, Paris, France)
LAG-3 (Adipogen, SanDiego, USA)

Method

P815 tumor cells were subcutaneously inoculated to DBA/2 mice in an amount of $5 \times 10^5$ cells per mouse. The day of inoculation was specified as Day 0. On Day 8, P1A CTL ($2.5 \times 10^5$ cells per mouse) were intravenously injected. On Day 9 and Day 16, an admixture of P1A peptide (50 μg per mouse) and an adjuvant in PBS was subcutaneously injected. Mice were divided into 9 groups each consisting of 5 mice and the following adjuvants were used, respectively.
Group 1: PBS (Control)
Group 2: IFA (50 μL/mouse)
Group 3: PT ($1 \times 10^8$/mouse)
Group 4: Poly IC (50 μg/mouse)
Group 5: Poly IC (50 μg/mouse)+CPG (10 μg/mouse)
Group 6: LAG-3 (1 μg/mouse)
Group 7: LAG-3 (1 μg/mouse)+Poly IC (50 μg/mouse)

Results

Changes in tumor size (mm$^3$) of all mice on and after Day 7 are shown in FIGS. 2 to 8.

In all of Groups 1 to 6, tumor sizes gradually increased and mice mostly died in the middle. The number of mice survived until Day 70 without increasing tumor size was 0 in Groups 2, 3 and 6, 1 in Groups 1 and 4, and 3 in Group 5; however, in Group 7, an increase in tumor size was not observed in all 5 mice and the mice survived until Day 115.

2. Infiltration of Immune Cells into Cancer Tissue

Cancer model mice were prepared by subcutaneously inoculating P815 tumor cells ($5 \times 10^5$ cells per mouse) to DBA/2 mice. The day of inoculation was specified as Day 0. On Day 8, P1A CTL ($2.5 \times 10^5$ cells per mouse) were intravenously injected. Day 9 and Day 14, an admixture of P1A peptide (50 μg per mouse) and an adjuvant in PBS was subcutaneously injected. The following adjuvants were used in respective mouse groups.
Group 1: IFA (50 μL/mouse)
Group 2: Poly IC (50 μg/mouse)
Group 3: LAG-3 (1 μg/mouse)
Group 4: LAG-3 (1 μg/mouse)+Poly IC (50 μg/mouse)

On Day 21, a tumor tissue was taken and slides of tumor tissue sections were prepared. Thereafter, a tissue image was observed by staining with hematoxylin-eosin; at the same time, cell nuclei and immune cells (CD4 cells and CD8 cells) were stained with a fluorescent dye.

The following reagents were used in the fluorescent tissue staining.
Cell nucleus: ProLongR Gold Antifade Reagent with DAPI (Invitrogen)
CD4 cell primary antibody: Rat Anti-Mouse CD4 Purified IgG2b. Clone: GK1.5 (eBioscience)
CD4 cell secondary antibody: Mouse monoclonal (2B 10A8) Anti-Rat IgG2b heavy chain (Alexa FluorR 647), (abcam)
CD8 cell primary antibody: Rat Anti-Mouse CD8α Purified IgG2a. Clone: 53-6.7 (eBioscience)
CD8 cell secondary antibody: Mouse monoclonal (2A 8F4) Anti-Rat IgG2a heavy chain (Alexa FluorR 488) (abcam)

Figure 9A:
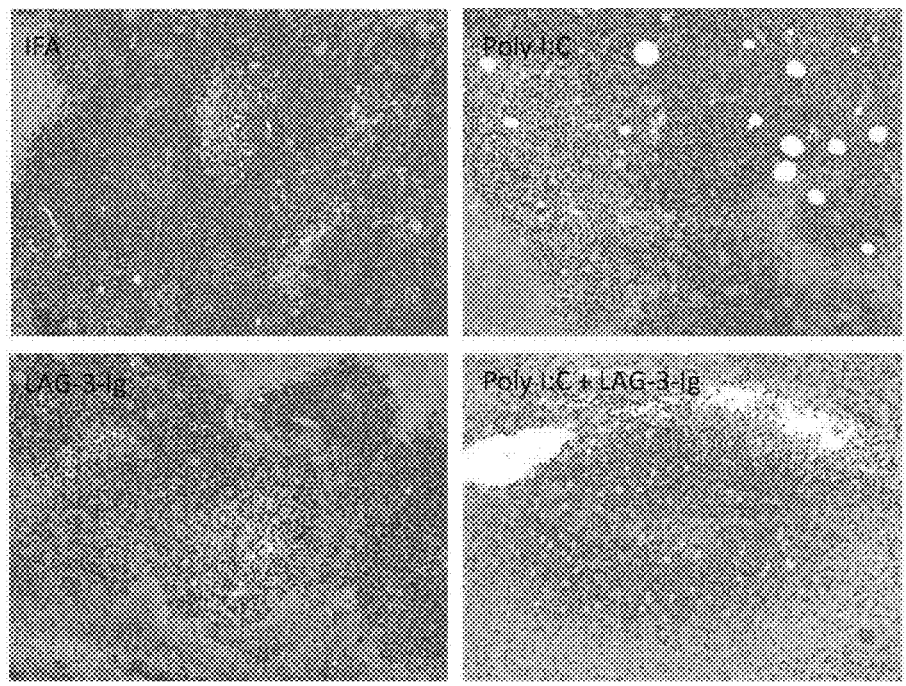
FIG. 9A shows images of a tumor tissue stained with hematoxylin-eosin in the same experiment as in FIG. 1.
Figure 9B:
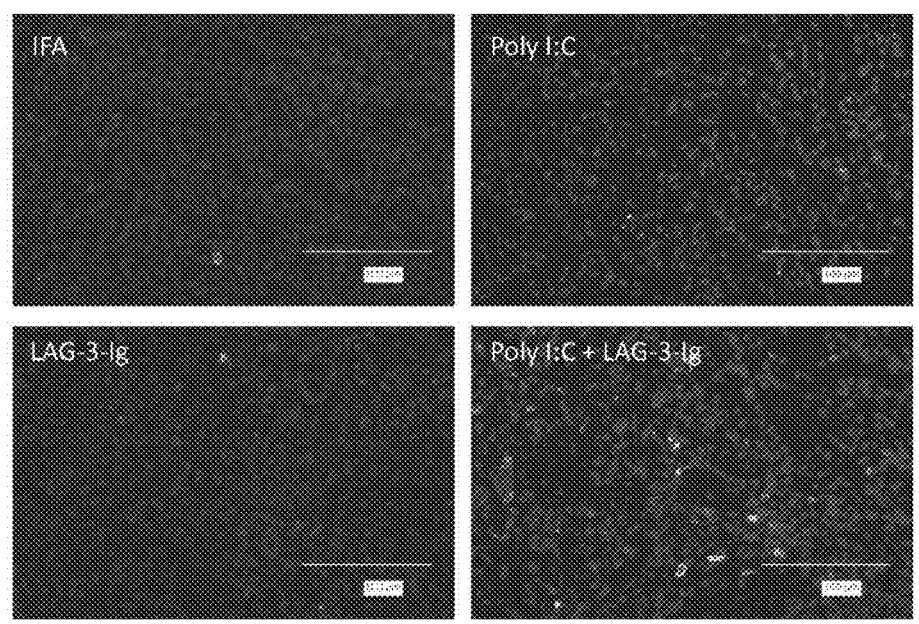
FIG. 9B shows images of cell nuclei and immune cells of a tumor tissue stained with a fluorescent dye in the same experiment as in FIG. 1.

Tissue images stained with hematoxylin-eosin are shown in FIG. 9A and images of cell nucleus and immune cells stained with a fluorescent dye are shown in FIG. 9B. When LAG-3 and poly IC were used in combination as an adjuvant, significant infiltration of CD4 cells and CD8 cells into a tumor tissue was observed.

3. Maintenance of Ability to Reject the Same Tumor in Mice Once Rejected a Tumor P815 tumor cells were subcutaneously inoculated to DBA/2 mice in an amount of $5 \times 10^5$ cells per mouse and used as cancer model mice. The day of inoculation was specified as Day 0. On Day 8, P1A CTL ($2.5 \times 10^5$ cells per mouse) were intravenously injected. On Day 9 and Day 14, an admixture of P1A peptide (50 μg per mouse) and an adjuvant in PBS was subcutaneously injected. As an adjuvant, LAG-3 (1 μg/mouse)+Poly IC (50 μg/mouse) was used.

Subsequently, to DBA/2 mice caused no increase in tumor size even if P815 tumor cells were inoculated, and determined as rejecting a tumor, and naive DBA/2 mice to which no treatment was applied, again P815 tumor cells ($1 \times 10^6$ cells per mouse) or L1210 tumor cells ($1 \times 10^6$ cells per mouse) were subcutaneously inoculated. To DBA/2 mice determined as rejecting a tumor, the tumor cells were again inoculated on Day 115 after the first inoculation of P815 tumor cells.

Figure 10:
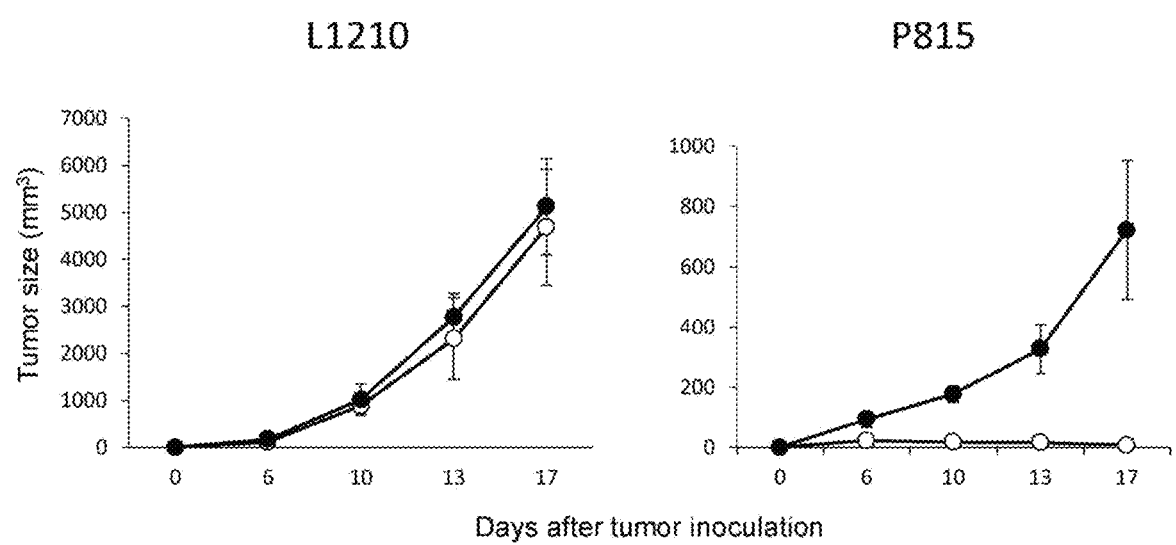
FIG. 10 is a graph showing the measurement results (increase) of tumor size after tumor cells were again inoculated to a mouse in which an increase in tumor size was once successfully suppressed by a cancer vaccine (LAG-3 and Poly I:C were used as adjuvants) in the same experiment as in FIG. 1.

FIG. 10 (left) shows changes in average tumor size (mm$^3$) of mice after inoculation of L1210 cells; whereas, FIG. 10 (right) shows changes in average tumor size (mm$^3$) of mice after inoculation of P815 cells. In both figures, open circle represents DBA/2 mice determined as a tumor rejection mice, and closed circle represents naive DBA/2 mice.

In naive DBA/2 mice, an increase in tumor size was observed even if either one of P815 cells and L1210 cells were inoculated. In contrast, in mice determined as rejecting a tumor growth of P815 cells, an increase in tumor size by inoculation of another type of tumor cells, i.e., L1210 cells, was observed; however, an increase in tumor size by P815 cell inoculation was not observed. It was confirmed that an ability to reject the same tumor is maintained.

4. Determination of the Proliferative Ability of Immune Cells and Measurement of the Cytokines in Cell Supernatant P815 tumor cells were subcutaneously inoculated to DBA/2 mice in an amount of $5\times10^5$ cells per mouse to prepare cancer model mice. The day of inoculation was specified as Day 0. On Day 8, PIA CTL ($2.5\times10^5$ cells per mouse) were intravenously injected. On Day 9 and Day 14, an admixture of PIA peptide (50 µg per mouse) and an adjuvant in PBS was subcutaneously injected. The following adjuvants were used in respective mice groups.

Group 1: IFA (50 µL/mouse)
Group 2: Poly IC (50 µg/mouse)
Group 3: LAG-3 (1 µg/mouse)
Group 4: LAG-3 (1 µg/mouse)+Poly IC (50 µg/mouse)

Of the lymph nodes in the axilla and inguinal region, the lymph node close to a tumor site was taken on Day 21 and immune cells were separated. The immune cells ($1.5\times10^5$ cells) and P815 cells ($4\times10^4$ cells) irradiated with 100Gy were co-cultured for 3 days.

Immune cell proliferative ability was determined by adding $^3$H-thymidine (37 KBq/well) to the culture supernatant and measuring the radioactivity of $^3$H-thymidine taken in the cells, 4 hours later.

The amounts of cytokines in the cell supernatant were measured by using Bio-Plex Pro mouse cytokine 23-Plex Immunoassay kit (BIO-RAD).

Figure 11A:
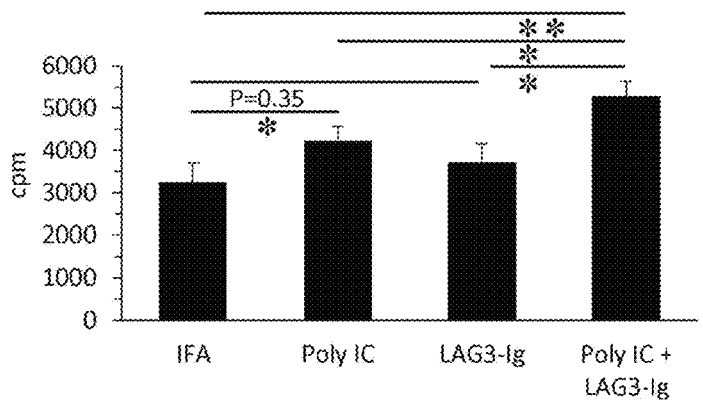
FIG. 11A is a graph showing the measurement results of proliferative ability of immune cells, which were prepared by taking a lymph node from a mouse inoculated with a cancer vaccine in the same experiment as in FIG. 1, separating the immune cells from the lymph node, and which were co-culturing with tumor cells previously inactivated by radiation exposure.
Figure 11B:
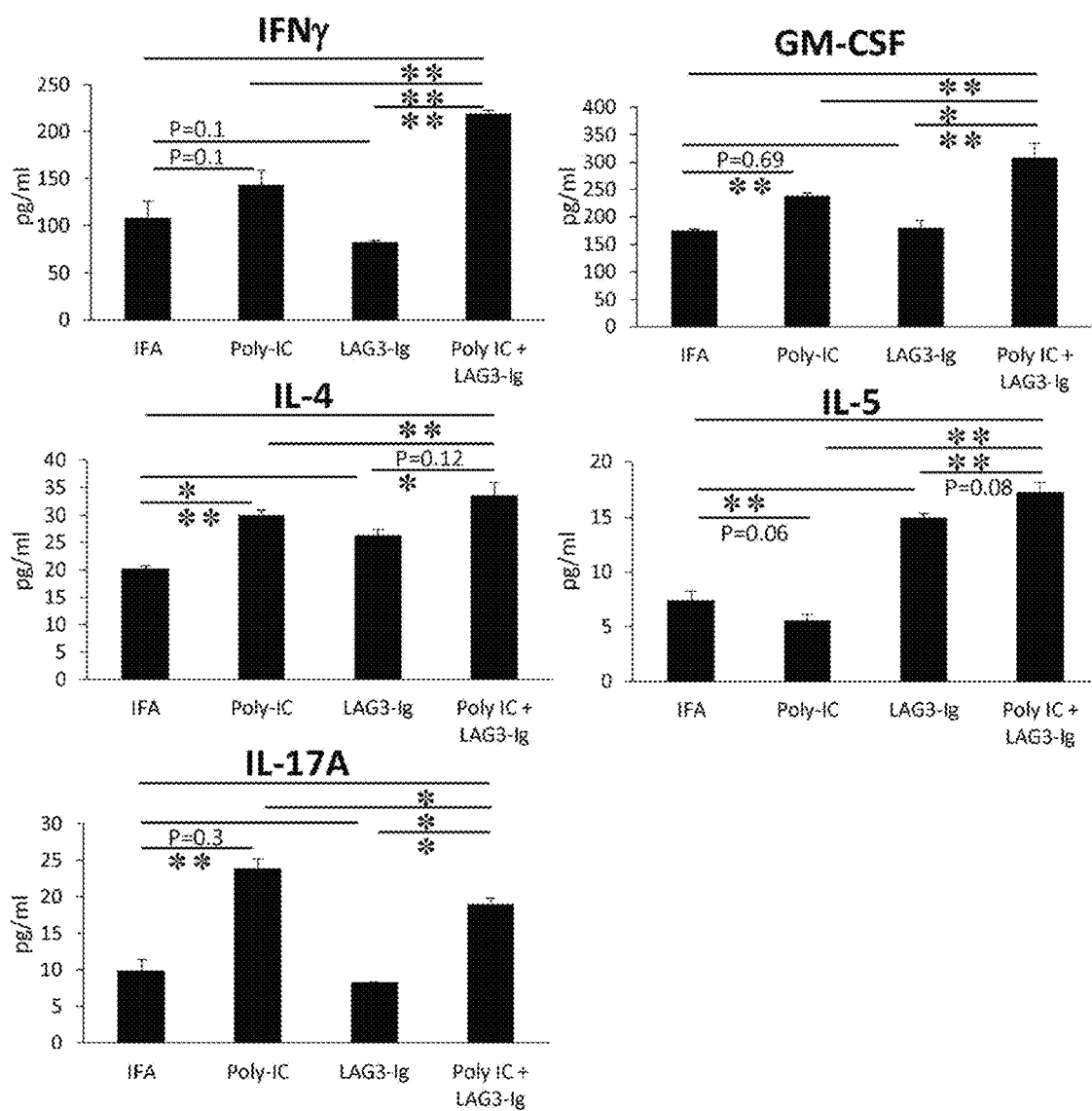
FIG. 11B shows graphs showing the measurement results of cytokines in the cell supernatant of the same co-culture as in the experiment in FIG. 11A.

Measurement results of immune cell proliferative ability are shown in FIG. 11A and measurement results of cytokines are shown in FIG. 11B.

In a case of using a combination of LAG-3 and poly IC as an adjuvant, immune cell proliferative ability increased. Among the cytokines, IFN-gamma, GM-CSF, IL-4, IL-5 and IL-17A were found to increase in production when LAG-3 and poly IC were used in combination as an adjuvant.

5. Measurement of Cell-Surface Marker Molecules of Immune Cells

P815 tumor cells were subcutaneously inoculated to DBA/2 mice in an amount of $5\times10^5$ cells per mouse to prepare cancer model mice. The day of inoculation was specified as Day 0. On Day 8, PIA CTL ($2.5\times10^5$ cells per mouse) were intravenously injected. On Day 9 and Day 14, an admixture of PIA peptide (50 µg per mouse) and an adjuvant in PBS was subcutaneously injected. The following adjuvants were used in respective mice groups.

Group 1: IFA (50 µL/mouse)
Group 2: Poly IC (50 µg/mouse)
Group 3: LAG-3 (1 µg/mouse)
Group 4: LAG-3 (1 µg/mouse)+Poly IC (50 µg/mouse)

Of the lymph nodes in the axilla or inguinal region, the lymph node close to a tumor site was taken on Day 21, CD8 and Vα 8.3 expression positive cell group (killer T cells) or CD4 and Vα 8.3 expression positive cell group (helper-T cells) were collected.

Expression levels of cell-surface marker molecules (on CD4 cells and CD8 cells), i.e., PD-1, BTLA, TIGIT and LAG-3, were measured. As antibodies against the cell surface marker molecules, the following molecules were used.

PD-1: Anti-mouse CD279 (PD-1) PE. Clone: J43 (eBioscience)
BTLA: Anti-mouse CD272 (BTLA) PE. Clone: 8F4 (eBioscience)
TIGIT: PE anti-mouse TIGIT (Vstm3) Antibody. Clone: 1G9 (BioLegend)
LAG-3: Anti-mouse CD223 (Lag-3) PE. Clone: eBioC9B7W (C9B7W) (eBioscience)

Figure 12A:
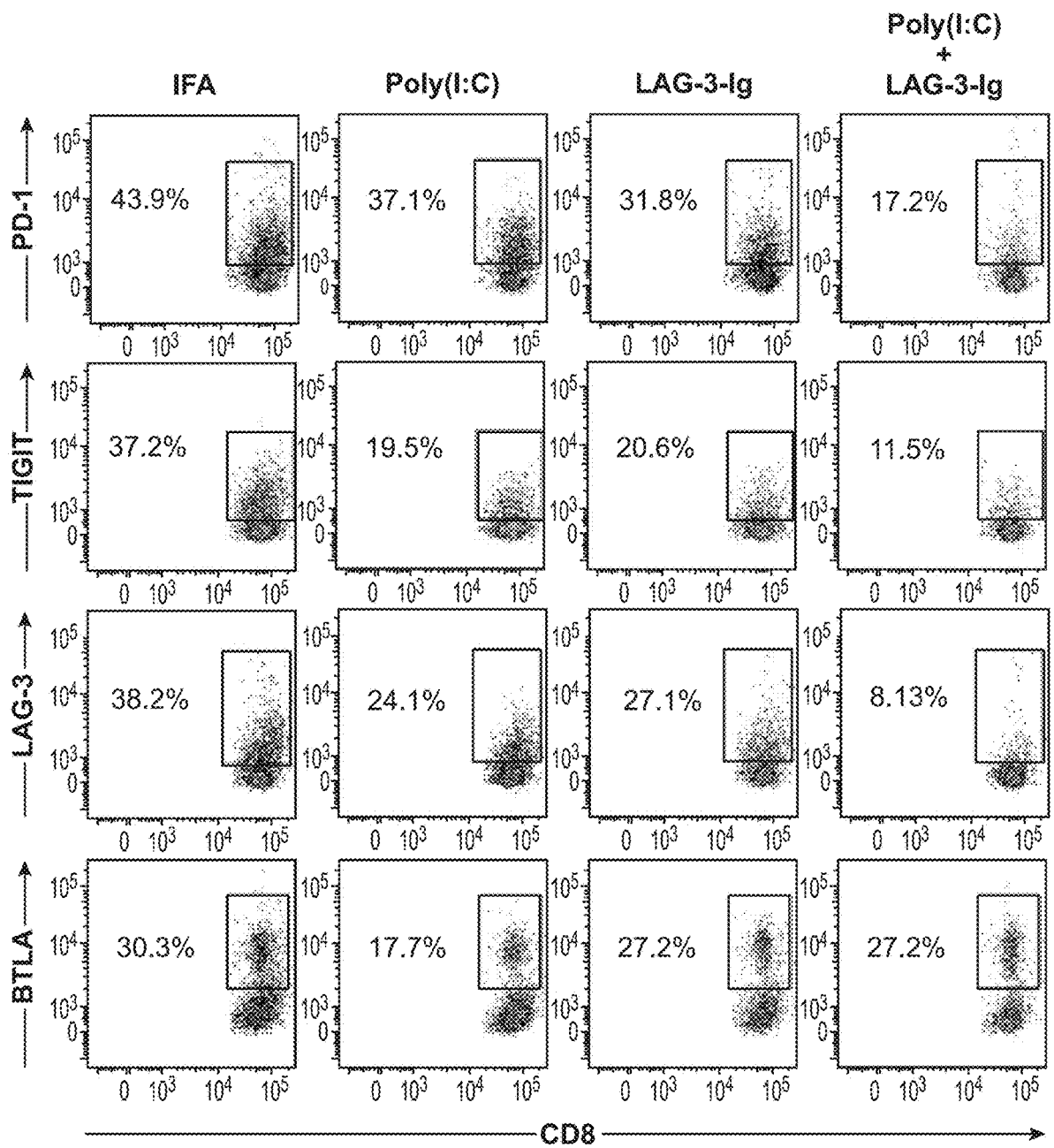
FIG. 12A shows the measurement results of expression of cell surface marker molecules, PD-1, BTLA, TIGIT and LAG-3, present on the surface of CD8 positive immune cells, which were prepared by taking a lymph node from a mouse inoculated with a cancer vaccine in the same experiment as in FIG. 1 and separating the immune cells from the lymph node.
Figure 12B:
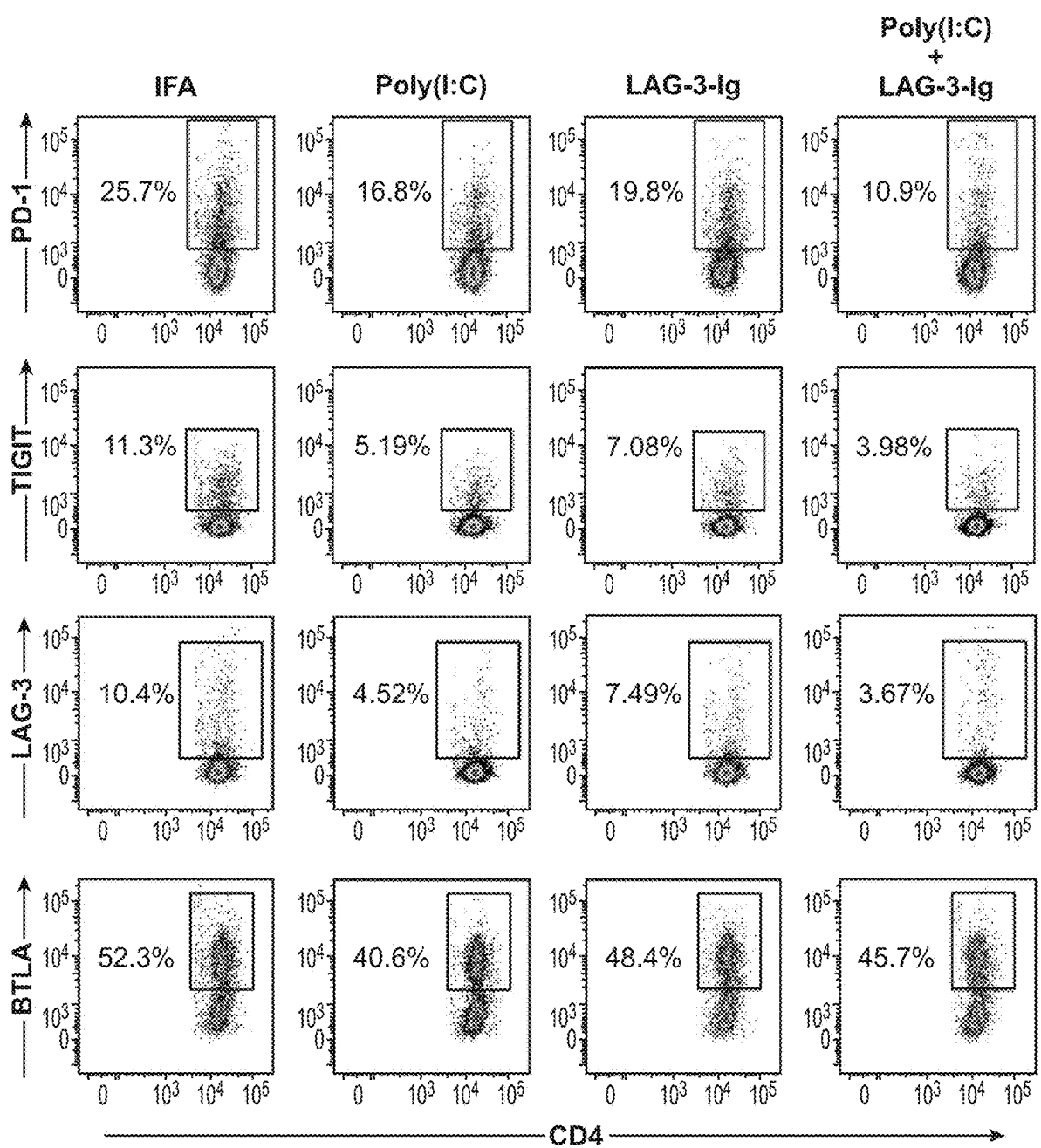
FIG. 12B shows the measurement results of expression of cell surface marker molecules, PD-1, BTLA, TIGIT and LAG-3, present on the surface of CD4 positive immune cells, which were prepared by taking a lymph node from a mouse inoculated with a cancer vaccine in the same experiment as in FIG. 1 and separating the immune cells from the lymph node.

The results of CD8 cells are shown in FIG. 12A and the results of CD4 cells are shown in FIG. 12B.

When a combination of LAG-3 and poly IC was used as an adjuvant, significant decreases in expression level of PD-1, TIGIT and LAG-3 were observed both in CD4 positive cells and CD8 positive cells; however, the decrease in expression level of BTLA was low.

6. Measurement of Cytokines Using B16-F10 Melanoma Inoculation Model Mice

To C57BL/6 mice, B16-F10 melanoma cells ($1\times10^5$ cells per mouse) were subcutaneously inoculated to prepare cancer model mice. The day of inoculation was specified as Day 0. On Day 8, an admixture of gp100 peptide (50 µg per mouse) and an adjuvant in PBS was subcutaneously injected. The following adjuvants were used in respective mice groups. The amino acid sequence of gp100 peptide is represented by KVPRNQDWL (SEQ. ID No: 2).

Group 1: IFA (50 µL/mouse)
Group 2: Poly IC (50 µg/mouse)
Group 3: LAG-3 (1 µg/mouse)
Group 4: LAG-3 (1 µg/mouse)+Poly IC (50 µg/mouse)

Of the lymph nodes in the axilla or inguinal region, the lymph node close to a tumor site (or both lymph nodes) was taken on Day 14 and immune cells were separated. The immune cells ($3\times10^5$ cells per well) were cultured in the presence of gp100 peptide (10, 5, 2.5, or 0 µg/mL).

Immune cell proliferative ability was determined by adding $^3$H-thymidine (37 KBq/well) to the culture supernatant and measuring the radioactivity of $^3$H-thymidine incorporated in the cells in the final 10 hours of the culture period of 3 days.

The IFN-gamma production amount in the cell supernatant obtained by culturing 3 days in the presence of gp100 peptide (10 µg/m) was measured by Bio-Plex Pro mice cytokine 23-Plex Immunoassay kit (BIO-RAD).

Figure 13A:
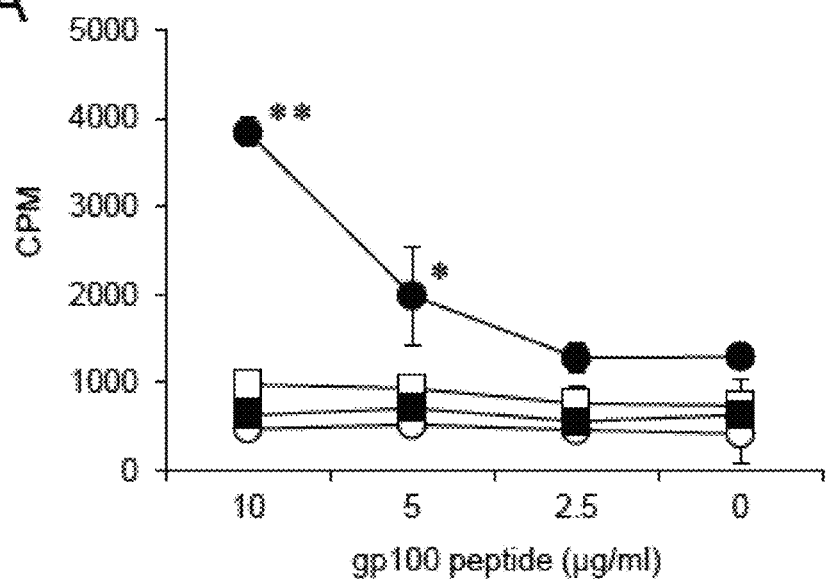
FIG. 13A is a graph showing measurement results of proliferative ability of immune cells.
Figure 13B:
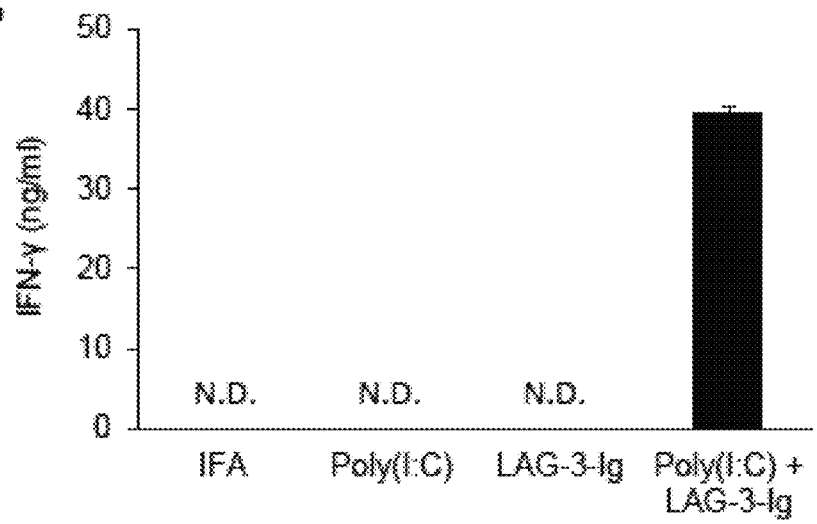
FIG. 13B is a graph showing measurement results of FN-gamma production.
Figure 14:
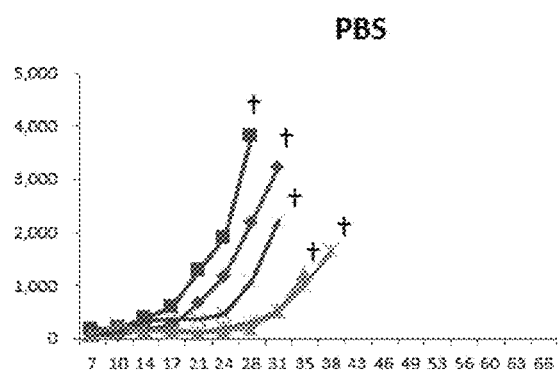
FIG. 14 is a graph showing changes in tumor size of Group 1, in which PBS was used as a control.
Figure 15:
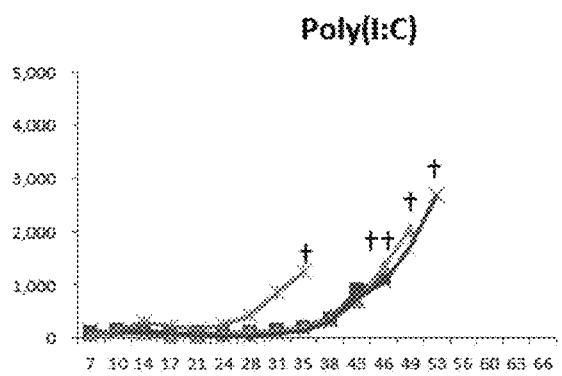
FIG. 15 is a graph showing changes in tumor size of Group 2, in which Poly I:C was used as an adjuvant.
Figure 16:
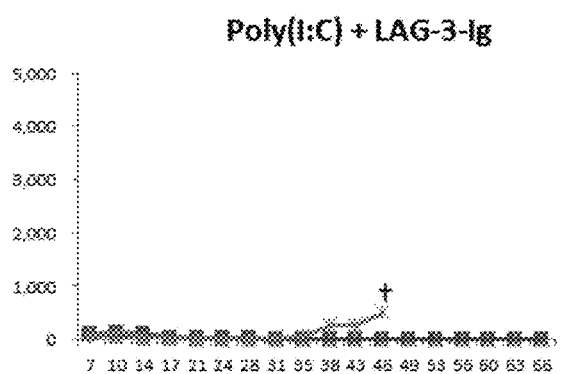
FIG. 16 is a graph showing changes in tumor size of Group 3, in which LAG-3 and Poly I:C were used as adjuvants.
Figure 17:
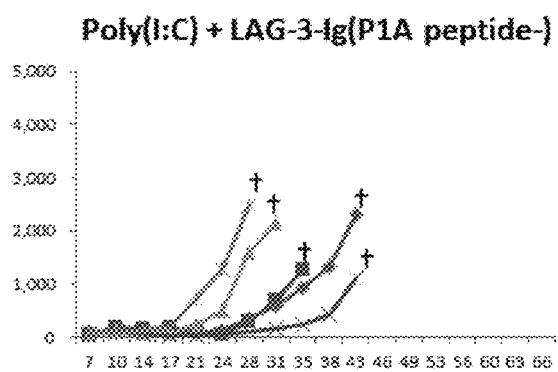
FIG. 17 is a graph showing changes in tumor size of Group 4, in which LAG-3 and Poly I:C alone were used without using PIA peptide.
Figure 18:
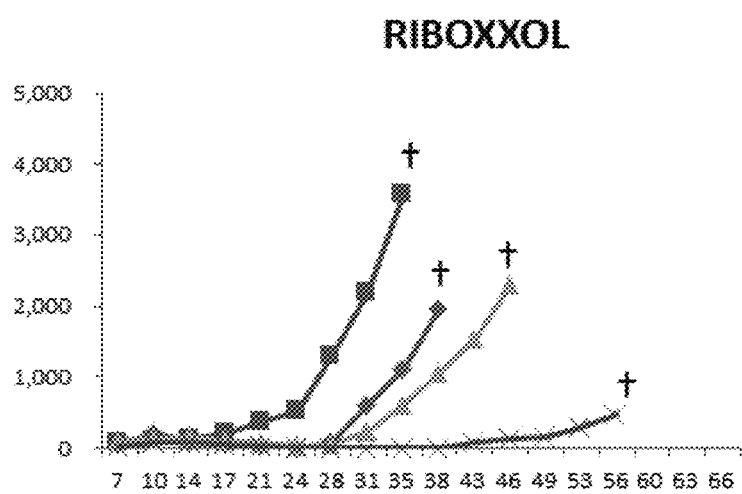
FIG. 18 is a graph showing changes in tumor size of Group 5, in which RIBOXXOL was used as an adjuvant.
Figure 19:
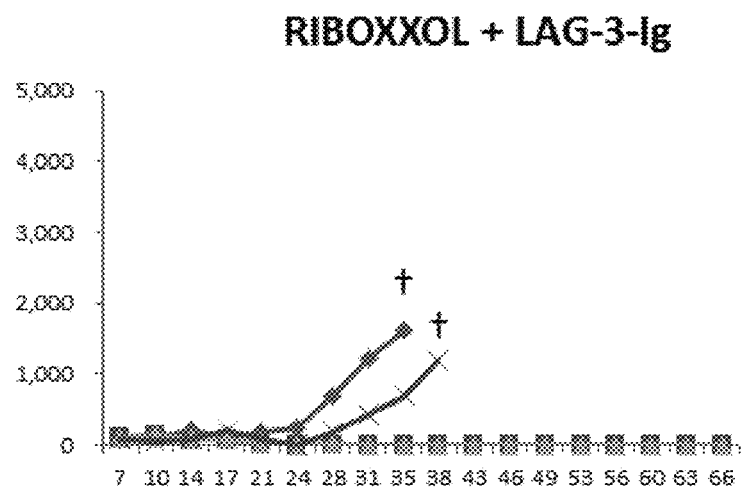
FIG. 19 is a graph showing changes in tumor size of Group 6, in which a combination of LAG-3 and RIBOXXOL was used as an adjuvant.
Figure 20:
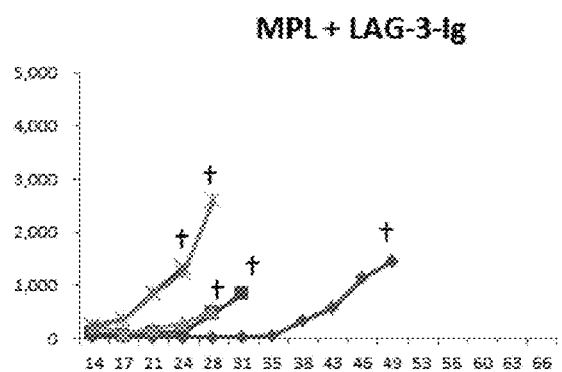
FIG. 20 is a graph showing changes in tumor size of Group 7, in which a combination of LAG-3 and MPL was used as an adjuvant.
Figure 21:
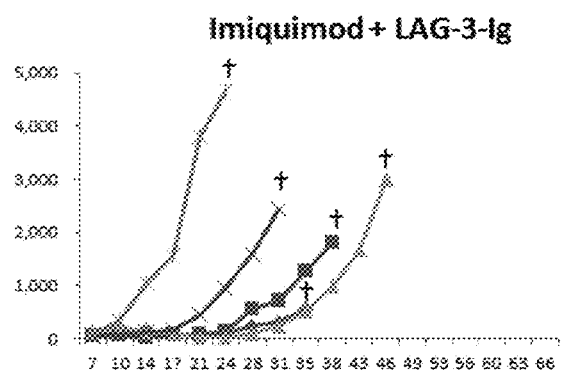
FIG. 21 is a graph showing changes in tumor size of Group 8, in which a combination of LAG-3 and Imiquimod was used as an adjuvant.
Figure 22:
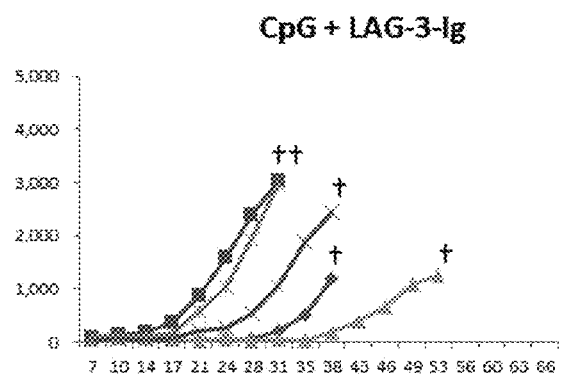
FIG. 22 is a graph showing changes in tumor size of Group 9, in which a combination of LAG-3 and CpG was used as an adjuvant.
Figure 23:
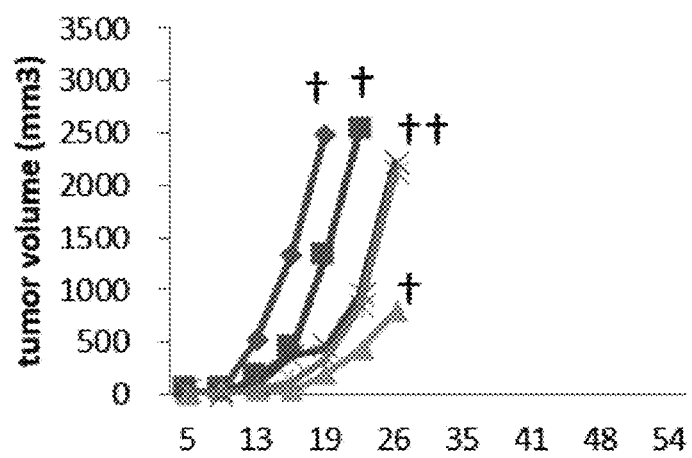
FIG. 23 is a graph showing changes in tumor size of Group 1, in which IFA was used as an adjuvant.
Figure 24:
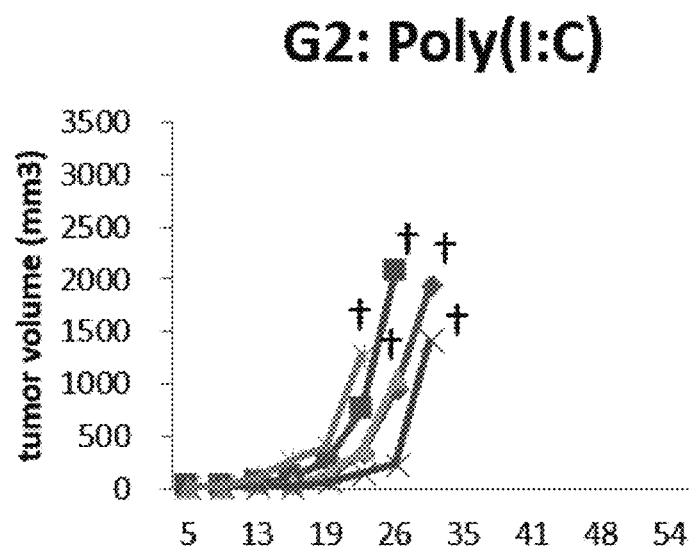
FIG. 24 is a graph showing changes in tumor size of Group 2, in which Poly I:C was used as an adjuvant.
Figure 25:
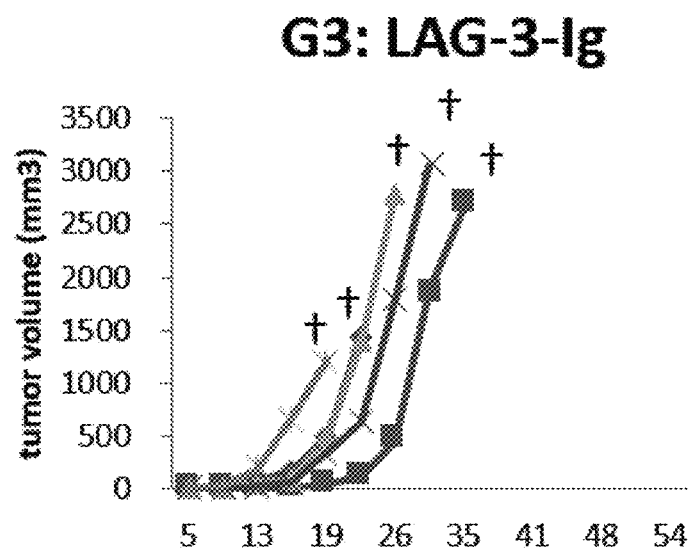
FIG. 25 is a graph showing changes in tumor size of Group 3, in which LAG-3 was used as an adjuvant.
Figure 26:
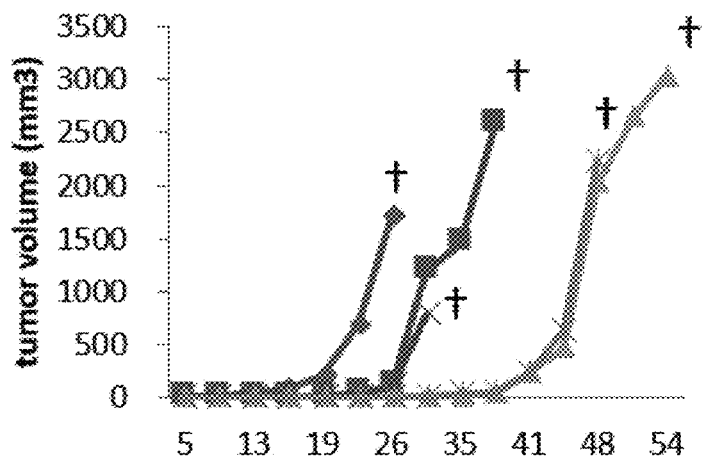
FIG. 26 is a graph showing changes in tumor size of Group 4, in which LAG-3 and Poly I:C were used as adjuvants.

Measurement results of immune cell proliferative ability are shown in FIG. 13A and measurement results of IFN-gamma production amount are shown in FIG. 13B. In FIG. 13A, closed circle represents the results of Group 1, open rectangle Group 2, closed rectangle Group 3 and open circle Group 4.

Even if B16-F10 melanoma inoculation model mice were used, if a combination of LAG-3 and poly IC was used as an adjuvant, an increase of immune cell proliferative ability specific to gp100 tumor antigen and an increase of IFN-gamma production were observed.

It was confirmed that when a combination of LAG-3 and poly IC was used as an adjuvant, a significant activation effect on the immune system can be exerted regardless of the tumor model system and the type of peptide serving as an immune antigen.

7. Suppression Effect of Tumor Growth by Immunoadjuvant Combination

The following substances were used as adjuvants.
Poly I:C (TLR3 agonist) (Invivogen, SanDiego, USA)
RIBOXXOL (TLR3 agonist) (Riboxx, Radebeul, Germany)
MPL (TLR4 agonist) (Invivogen, SanDiego, USA)
Imiquimod (TLR7/8 agonist) (Invivogen, SanDiego, USA)
CpG (TLR9 agonist) (Invivogen, SanDiego, USA)
LAG-3 (Adipogen, SanDiego, USA)

P815 tumor cells were subcutaneously inoculated to DBA/2 mice in an amount of $5\times10^5$ cells per mouse to prepare cancer model mice. The day of inoculation was specified as Day 0. On Day 7, PIA CTL ($2.5\times10^5$ cells per mouse) were intravenously injected. Day 8 and Day 15, an admixture of PIA peptide (50 μg per mouse) and an adjuvant in PBS was subcutaneously injected. Mice were divided into 9 groups each consisting of 4 or 5 mice and the following adjuvants were used respectively.

Group 1: PIA peptide alone (control)
Group 2: Poly IC (50 μg/mouse)
Group 3: Poly IC (50 μg/mouse)+LAG-3 (1 μg/mouse)
Group 4: No PIA peptide, Poly IC (50 μg/mouse)+LAG-3 (1 μg/mouse) alone
Group 5: RIBOXXOL (100 μg/mouse)
Group 6: RIBOXXOL (100 μg/mouse)+LAG-3 (1 μg/mouse)
Group 7: MPL (10 μg/mouse)+LAG-3 (1 μg/mouse)
Group 8: Imiquimod (50 μg/mouse)+LAG-3 (1 μg/mouse)
Group 9: CpG (10 μg/mouse)+LAG-3 (1 μg/mouse)

Change in tumor size ($mm^3$) with respect to all mice on and after Day 7 are shown in FIGS. 14 to 20.

In Group 1, 5 out of 5 mice all died up to Day 40. Four out of 5 mice in Group 2, 5 out of 5 mice in Group 3, 2 out of 5 mice in Group 4 and 1 out of 5 mice in Groups 5 to 7 survived. In addition, in Group 3, 3 out of 5 mice survived up to Day 66. A combination effect of adjuvants was demonstrated by comparing between Groups 2 to 4 and Groups 5 and 6. In Group 4 where PIA peptide was not administered, all mice died up to Day 43. It was demonstrated that administration of both an adjuvant and PIA peptide is preferable.

8. Tumor Growth Inhibitory Effect by Combination of Immuno-Adjuvants Using B16-F10 Melanoma Inoculation Model Mice To C57BL/6 mice, B16-F10 melanoma cells ($1\times10^5$ cells per mouse) were subcutaneously inoculated to prepare cancer model mice.

The day of inoculation was specified as Day 0. On Day 5 and Day 12, twice in total, an admixture of gp100 peptide (50 μg per mouse) and an adjuvant in PBS was subcutaneously injected. The following adjuvants were used in respective mice groups.

Group 1: IFA (50 μL/mouse)
Group 2: Poly IC (50 μg/mouse)
Group 3: LAG-3 (1 μg/mouse)
Group 4: LAG-3 (1 μg/mouse)+Poly IC (50 μg/mouse)

Changes in tumor size ($mm^3$) of all mice on and after Day 5 are shown in FIGS. 21 to 24. Five mice all died on Day 31 in Group 1, on Day 35 in Group 2 and on Day 37 in Group 3. In contrast, five mice died in Group 4 on Day 57. Compared to Group 1, a significant effect of extending survival time was not observed in Groups 2 and 3; however, the survival time of Group 4 was significantly extended compared to any one of Groups 1, 2 and 3.

SEQUENCE LISTING FREE TEXT

SEQ. ID No: 1 represents the amino acid sequence of PIA peptide.
SEQ. ID No: 2 represents the amino acid sequence of gp100 peptide.

The invention claimed is:

1. A pharmaceutical composition comprising
Poly I:C or a salt thereof and
a fusion protein of lymphocyte activation gene 3 (LAG-3) protein and IgG.

2. The pharmaceutical composition according to claim 1, consisting of
a preparation comprising Poly I:C or a salt thereof and
a preparation comprising a fusion protein of LAG-3 protein and IgG,
wherein the two preparations are formulated for combined administration.

3. The pharmaceutical composition according to claim 1, further comprising at least one cancer-antigen derived peptide.

4. The pharmaceutical composition according to claim 3, consisting of
a preparation comprising Poly I:C or a salt thereof,
a preparation comprising a fusion protein of LAG-3 protein and IgG, and
a preparation comprising at least one type of cancer-antigen derived peptide
wherein the three preparations are formulated for combined administration.

5. The pharmaceutical composition according to claim 3, comprising two or more cancer-antigen derived peptides.

* * * * *